United States Patent
Sarkar

(10) Patent No.: US 10,317,672 B2
(45) Date of Patent: Jun. 11, 2019

(54) EYE-TRACKING SYSTEM AND METHOD THEREFOR

(71) Applicant: ICSPI Corp., Waterloo (CA)

(72) Inventor: Niladri Sarkar, Waterloo (CA)

(73) Assignee: AdHawk Microsystems, Kitchener, Ontario (CA)

( * ) Notice: Subject to any disclaimer, the term of this patent is extended or adjusted under 35 U.S.C. 154(b) by 0 days.

(21) Appl. No.: 15/615,473

(22) Filed: Jun. 6, 2017

(65) Prior Publication Data

US 2017/0276934 A1 Sep. 28, 2017

Related U.S. Application Data

(63) Continuation-in-part of application No. 14/966,733, filed on Dec. 11, 2015.

(Continued)

(51) Int. Cl.
| | | |
|---|---|---|
| A61B 3/14 | (2006.01) | |
| A61B 3/10 | (2006.01) | |
| A61B 3/02 | (2006.01) | |
| A61B 3/00 | (2006.01) | |
| G02B 27/00 | (2006.01) | |
| G02B 26/08 | (2006.01) | |
| G01P 3/36 | (2006.01) | |

(Continued)

(52) U.S. Cl.
CPC .......... *G02B 27/0093* (2013.01); *A61B 3/113* (2013.01); *A61B 3/15* (2013.01); *G01B 11/002* (2013.01); *G01P 3/36* (2013.01); *G02B 26/0833* (2013.01); *G02B 26/0866* (2013.01); *G02B 26/101* (2013.01)

(58) Field of Classification Search
CPC .......... A61B 3/103; A61B 3/113; A61B 3/14; A61B 3/1225; A61B 3/024; A61B 3/032; A61B 3/18; A61B 3/1015
USPC ........ 351/200, 205–206, 209–210, 221–223, 351/245–246
See application file for complete search history.

(56) References Cited

U.S. PATENT DOCUMENTS 5,638,176 A 6/1997 Hobbs et al.
5,805,267 A * 9/1998 Goldman ............. A61N 5/0618
351/200

(Continued)

OTHER PUBLICATIONS

Oak et al., "Development and Testing of a Multilevel Chevron Actuoator-Based Positioning System", "Journal of Microelectromechanical Systems", Dec. 2011, pp. 1298-1309, vol. 20, No. 6.

(Continued)

*Primary Examiner* — Dawayne Pinkney
(74) *Attorney, Agent, or Firm* — Kaplan Breyer Schwarz, LLP

(57) ABSTRACT

A system for tracking eye location is disclosed. Systems in accordance with the present invention include a scanner for sweeping a first optical signal across the surface of an eye, a detector for detecting a second optical signal reflected from the eye, and a detection circuit for determining a maximum intensity in the second optical signal. In operation, the scanner sweeps the first optical signal over the surface of the eye while the detection circuitry determines a plurality of intensity maxima in the second optical signal. The time between the intensity maxima during the sweep is indicative of the location of the cornea within the eye surface.

8 Claims, 19 Drawing Sheets

Related U.S. Application Data

(60) Provisional application No. 62/345,926, filed on Jun. 6, 2016, provisional application No. 62/090,705, filed on Dec. 11, 2014, provisional application No. 62/181,276, filed on Jun. 18, 2015, provisional application No. 62/266,020, filed on Dec. 11, 2015.

(51) Int. Cl.
  *G01B 11/00* (2006.01)
  *A61B 3/113* (2006.01)
  *A61B 3/15* (2006.01)
  *G02B 26/10* (2006.01)

(56) References Cited

U.S. PATENT DOCUMENTS

| | | | |
|---|---|---|---|
| 5,909,078 A | 6/1999 | Wood et al. | |
| 6,275,320 B1 | 8/2001 | Dhuler et al. | |
| 6,333,583 B1 | 12/2001 | Mahadevan et al. | |
| 6,806,991 B1 | 10/2004 | Sarkar et al. | |
| 6,877,316 B1 | 4/2005 | Sarkar et al. | |
| 7,538,470 B2 | 5/2009 | Sarkar | |
| 8,402,561 B2 | 3/2013 | Sarkar | |
| 8,824,779 B1* | 9/2014 | Smyth | G06K 9/0061 382/100 |
| 8,955,973 B2 | 2/2015 | Raffle et al. | |
| 2002/0041259 A1 | 4/2002 | Lewis et al. | |
| 2003/0121260 A1 | 7/2003 | Sinclair | |
| 2003/0146901 A1* | 8/2003 | Ryan | G06F 3/013 345/158 |
| 2007/0001248 A1 | 1/2007 | Geisberger et al. | |
| 2007/0159599 A1* | 7/2007 | Yamada | G02B 27/0093 351/211 |
| 2007/0268808 A1 | 11/2007 | Culver et al. | |
| 2009/0139340 A1 | 6/2009 | King et al. | |
| 2010/0149506 A1 | 6/2010 | De Vries | |
| 2013/0021656 A1 | 1/2013 | Albus et al. | |
| 2014/0375545 A1* | 12/2014 | Ackerman | G06F 3/017 345/156 |
| 2015/0047078 A1 | 2/2015 | Sarkar et al. | |

OTHER PUBLICATIONS

Alex Man Ho Kwan et al., "Improved Designs for an Electrothermal In-Plane Microactuator", "Journal of Microelectromechanical Systems", Jun. 1, 2012, pp. 586-595, vol. 21, No. 3, Publisher: IEEE.

Long Que et al., "Bent-Beam Electrothermal Actuators—Part I: Single Beam and Cascaded Devices", "Journal of Microelectromechanical Systems", Jun. 1, 2001, pp. 247-254, vol. 10, No. 2, Publisher: IEEE.

G. K Fedder et al, "Laminated High-Aspect-Ratio Microstructures in a Conventional DMOS Process", Jun. 1, 1996, vol. 0/7803-298-6/96, Publisher: IEEE.

J. C. Hulme et al., "Fully integrated hybrid silicon two dimensional beam scanner", DOI:10.1364/OE.23.005861, "Optics Express", Mar. 9, 2015, vol. 23, No. 5, Publisher: Optical Society of America, Published in: Santa Barbara, California.

Peter J. Gilgunn et al, "CMOS-MEMS Lateral Electrothermal Actuators", 10.1109/JMEMS.2007.911373, "Journal of Microelectromechanical Systems", Oct. 1, 2007, vol. 1057-7157, Publisher: IEEE, Published in: Pittsburgh, PA.

Di Liang et al., "Hybrid Integrated Platforms for Silicon Photonics", doi: 10.3390/ma3031782, ISSN 1996-1944, www.mdpi.com/journal/materials, "Materials", Mar. 12, 2010, vol. 3, 1782-1802.

Final Rejection dated Mar. 27, 2018 for U.S. Appl. No. 14/966,733.

* cited by examiner

EYE-TRACKING SYSTEM AND METHOD THEREFOR

CROSS REFERENCE TO RELATED APPLICATIONS

This application claims the benefit of U.S. Provisional Patent Application Ser. No. 62/345,926 and is a continuation-in-part of U.S. patent application Ser. No. 14/966,733 filed 11 Dec. 2015, which claims the benefit of U.S. Provisional Application Ser. No. 62/090,705, filed Dec. 11, 2014, entitled "Electro-Thermo-Mechanical Optical Scanner Suitable for Display, Imaging, or Object Tracking Applications," U.S. Provisional Application Ser. No. 62/181,276, filed Jun. 18, 2015, entitled "Near-Eye Display and Method Therefor," and U.S. Provisional Application Ser. No. 62/266,020, filed Dec. 11, 2015, entitled "System for Tracking Eye Position and Method Therefor," each of which is incorporated herein by reference as if set forth at length herein. If there are any contradictions or inconsistencies in language between this application and one or more of the cases that have been incorporated by reference that might affect the interpretation of the claims in this case, the claims in this case should be interpreted to be consistent with the language in this case.

FIELD OF THE INVENTION

The present invention relates to object-tracking systems in general, and, more particularly, to eye-tracking systems.

BACKGROUND OF THE INVENTION

The movement of the human eye can reveal a wealth of information about the neural mechanisms of the brain and vision, as well as an individual's neurological health, ocular health, interests, and state-of-mind. In addition, the tracking of eye movement can be used to improve/augment human-computer interaction, enable gaze-based man-machine interfaces, and enhance how we interact with wearable technology. For example, gaze tracking, which relies on eye tracking, enables many augmentative alternative communication (AAC) devices that improve the ability for individuals lacking speech capability and/or motor skills (e.g., amyotrophic lateral sclerosis (ALS) patients or those with spinal cord injuries) to interact with the world around them.

In recent years, eye-tracking technology has become more sophisticated and is increasingly being directed toward non-health-related uses, such as improving advertising effectiveness, determining optimal product placement, improving package design, augmenting the automotive driving experience, gaming and virtual reality (VR) systems, military training and effectiveness augmentation, athletic training, and the like. For advertising and/or product placement applications, for example, the activity of a subject's eyes is tracked while target stimuli (e.g., web sites, commercials, magazine ads, newspapers, product packages, etc.) are presented. The recorded eye-tracking data is statistically analyzed and graphically rendered to reveal specific visual patterns. By examining fixations, saccades, pupil dilation, blinks and a variety of other behaviors, the effectiveness of a given medium or product can be determined.

Helmet-integrated eye-trackers could potentially improve the ability of a fighter pilot to better control an aircraft and react to high-speed battle conditions while in flight. Eye tracking in this scenario may provide capabilities to enhance interaction between the pilot and vehicle. In addition, post-flight analysis of the pilot's gaze could be useful for training purposes. Further, in-flight health monitoring is possible by tracking changes in the geometry of the eye due to swelling caused by rapid changes in pressure.

Unfortunately, conventional eye-trackers are slow, bulky, invasive, and/or restrictive for the user. This makes them difficult, if not impossible to use in many of the applications discussed above. In addition, conventional systems generally require cameras and imaging processing software. As a result, they tend to be expensive, slow, and power hungry. Furthermore, they typically exhibit significant lag between eye movement and measured eye position, which degrades the user experience in VR applications. It is possible to improve the resolution and speed of such eye tracking systems but, to date, these improvements have come at the expense of user mobility and added system cost.

Eye coils mounted directly on the eye have been used to track eye position with high accuracy; however, they require operation within a magnetic field, which restricts the applications in which they can be used. Further, since they are placed directly on the eyeball, they can only be used for limited times due to eye safety and vision impairment issues.

Electro-oculograms enable the position of the cornea through closed eyelids; however, they are subject to blink artifacts and signal noise. In addition, they are relatively inaccurate. Further, they require electrodes to be attached in or near the eye. As a result, electro-oculograms are relatively unattractive in many applications.

Systems for tracking the limbus (i.e., the boundary between the white of the eye and the dark iris) have been used for eye tracking as well. Unfortunately, such limbal-tracking systems are cumbersome, difficult to align and calibrate, and have poor sensitivity unless used at short range.

Perhaps the most common eye-tracking systems are video-based systems, such as image-processing systems described in U.S. Pat. No. 8,955,973. In these systems, a picture of the surface of the eye is taken under infrared (IR) illumination and captured by a two-dimensional image sensor. The picture reveals the location of the corneal reflection and the pupil of the eye. Using complex image processing, a vector from the center of the corneal reflection to the center of the pupil is calculated and this vector forms the basis of an estimate of the direction of the user's gaze. Video-based eye trackers can be used remotely or worn by the subject.

Unfortunately, such eye-tracking systems are slow, bulky, restrictive for the user, and expensive. Wearable systems are bulky and heavy, making them quite uncomfortable for extended use. Remote systems require careful positioning and alignment, which can be easily disrupted during operation. In addition, the reliance on video capture and image processing leads to the need for good lighting conditions. Further, video capture is difficult to perform tracking through spectacles due to front surface reflections.

As an alternative to video-based systems, some conventional eye-tracking systems project a grid of structured light onto the surface of the eye. Unfortunately, an image of the eye surface must still be captured and analyzed via image processing to estimate eye position. As a result, while such systems typically require less computational complexity than video-based eye-trackers, they still demand significant computational and energy resources.

A low-cost, high resolution, low power, high-speed, robust eye-tracking system would, therefore, be a significant advance in the state of the art.

SUMMARY OF THE INVENTION

The present invention enables eye tracking without some of the costs and disadvantages of eye-tracking systems of the prior art. Furthermore, inventive concepts of the present invention can be employed to enable additional tracking capabilities, such as head tracking, finger tracking, agile free-space communications links, single-fiber endoscopy, and the like. Embodiments of the present invention are particularly well suited for use in applications such as heads-up displays, virtual and augmented reality systems, weapons targeting systems, automotive cabin control, collision avoidance systems, advertising design and placement effectiveness studies, website design, pay-per-gaze advertising, athletic training programs, health monitoring systems, medical research, optometry, augmentative alternative communications systems, wearable sensor systems, and environmental control systems.

According to one aspect of the present invention eye—or other appendage or object—movement may be tracked by a method comprising generating an intensity profile of the eye/appendage/object being tracked; and determining eye/appendage/object movement from the generated intensity profile. More specifically, such operations may include generating a second intensity profile of the eye/appendage/object; and comparing the intensity profile to the second intensity profile; wherein said eye/appendage/object movement is determined from any comparative differences in the intensity profile(s).

An illustrative embodiment of the present invention is an eye-tracking system that is suitable for mounting on the frame of a pair of eye glasses. The system includes a laser, a two-dimensional scanning mirror, a discrete detector, and a detection circuit, where the two-dimensional scanning mirror and detector are mounted on opposite sides of one lens of the eye glasses. The laser and mirror are arranged on the eyeglass frame such that they collectively interrogate a scan region on the surface of an eye of a subject with an optical input signal that is characterized by a far-field pattern having a global intensity maximum region.

In operation, the laser provides the optical input signal to the scanning mirror, which sweeps the input signal over the scan region of the eye over which the cornea is located. In the illustrative embodiment, the scanning mirror first sweeps the input signal back and forth, at a constant rate, along a first linear path aligned with the horizontal axis of the eye. The cornea reflects the input signal as a reflected signal, which is incident on the detector. The detector provides an electrical signal whose magnitude represents the average intensity of the reflected signal impinging on its surface. As the input signal sweeps across the eye in the forward direction, a first peak in the intensity of the reflected signal arises when the input signal is incident on at least a portion of the cornea of the eye at which the curvature of the cornea directs the reflected signal towards the detector. As the input signal is swept back across the eye in the reverse direction, a second peak in the intensity of the reflected signal arises when the input signal is again incident on the cornea. By sweeping the input signal across the eye at a constant rate, the time delay between the first and second peaks can be used to estimate the horizontal position of the cornea within the scan region of the eye being scanned. Once this horizontal position is determined, the scanning mirror scans the input beam back and forth along a second linear path aligned with the vertical axis of the eye, where the second linear path is positioned at the horizontal position of the cornea. This back and forth vertical sweep again gives rise to a pair of peaks whose timing is used to estimate the vertical position of the cornea within the eye.

In some embodiments, the two-dimensional position of the cornea within the scan region is estimated via scanning the input beam back and forth along a first linear path aligned with one of the horizontal or vertical axis of the eye while a hill-climbing control method is used in the orthogonal axis to substantially maximize the peak amplitude of the electrical signal provided by the detector.

In some embodiments, the input signal is swept within the scan region in a two-dimensional path, such as a circular path, an elliptical path, a Lissajous path, a rhodonea path, and the like. In some such embodiments, only peak locations (not intensities) may be used to reveal eye position, and only steady-state sinusoidal functions are applied to the scanning mirror.

In some embodiments, the scanning mirror includes an optical element that converts the input signal into a light pattern, such a dot or cross, on the eye. In some of these embodiments, the optical element is a diffractive element, such as a Fresnel lens, holographic element, etc., which is formed on the surface of the scanning mirror.

In some embodiments, a calibration procedure is run before the system is used to track eye position. In some embodiments, a calibration procedure is run periodically while the system is used to track eye position. Calibration procedures in accordance with the present invention include measuring the position of the scanning mirror while the user looks at each of one or more spots on a screen at a fixed location.

In some embodiments, the scanning mirror includes one isothermal actuator for controlling the angle of a reflective surface about an axis. In some embodiments, an isothermal actuator is used to control the angle of the reflective surface about each of a pair of orthogonal axes.

In some embodiments, the position of the scanning mirror is controlled via pulse-width modulated drive signals.

An embodiment of the present invention is a system for estimating the corneal vector of an eye, the system comprising: a first source operative for providing a first optical signal, the first optical signal being characterized by a far-field pattern having a global intensity maximum; a first scanner operative for scanning the first optical signal within a scan region on the surface of the eye, the scan region including a surface feature of the eye; a first detector that is a discrete detector, the first detector being operative for providing a first electrical signal based on a second optical signal that includes a portion of the first optical signal reflected from at least a portion of the scan region; and a detection circuit operative for determining at least one maximum in the first electrical signal.

Another embodiment of the present invention is a system for estimating the corneal vector of an eye, the system comprising: a first source operative for providing a first optical signal, the first optical signal being characterized by a far-field pattern having a global intensity maximum; a first scanning mirror operative for scanning the first optical signal within a scan region on the surface of the eye; a first detector that is a discrete detector, the first detector being operative for providing a first electrical signal based on the detected intensity of a second optical signal that includes a portion of the first optical signal reflected from at least a portion of the scan region; a detection circuit operative for determining a first maximum in the first electrical signal at a first time and a second maximum in the first electrical signal at a second time; and a processor operative for estimating the location of the surface feature within the scan region based on the difference between the first time and second time.

Yet another embodiment of the present invention is a method for estimating the corneal vector of an eye, the method comprising: scanning a first optical signal within a scan region on the surface of the eye; receiving a second optical signal at a first detector that is a discrete detector, the second optical signal including a portion of the first optical signal that is reflected from at least a portion of the scan region; generating a first electrical signal based on the second optical signal, the first electrical signal being generated by the first detector; determining at least one maximum of the second optical signal; estimating the first position based on the at least one maximum; and estimating the corneal vector based on the first location.

DETAILED DESCRIPTION

Figure 1:
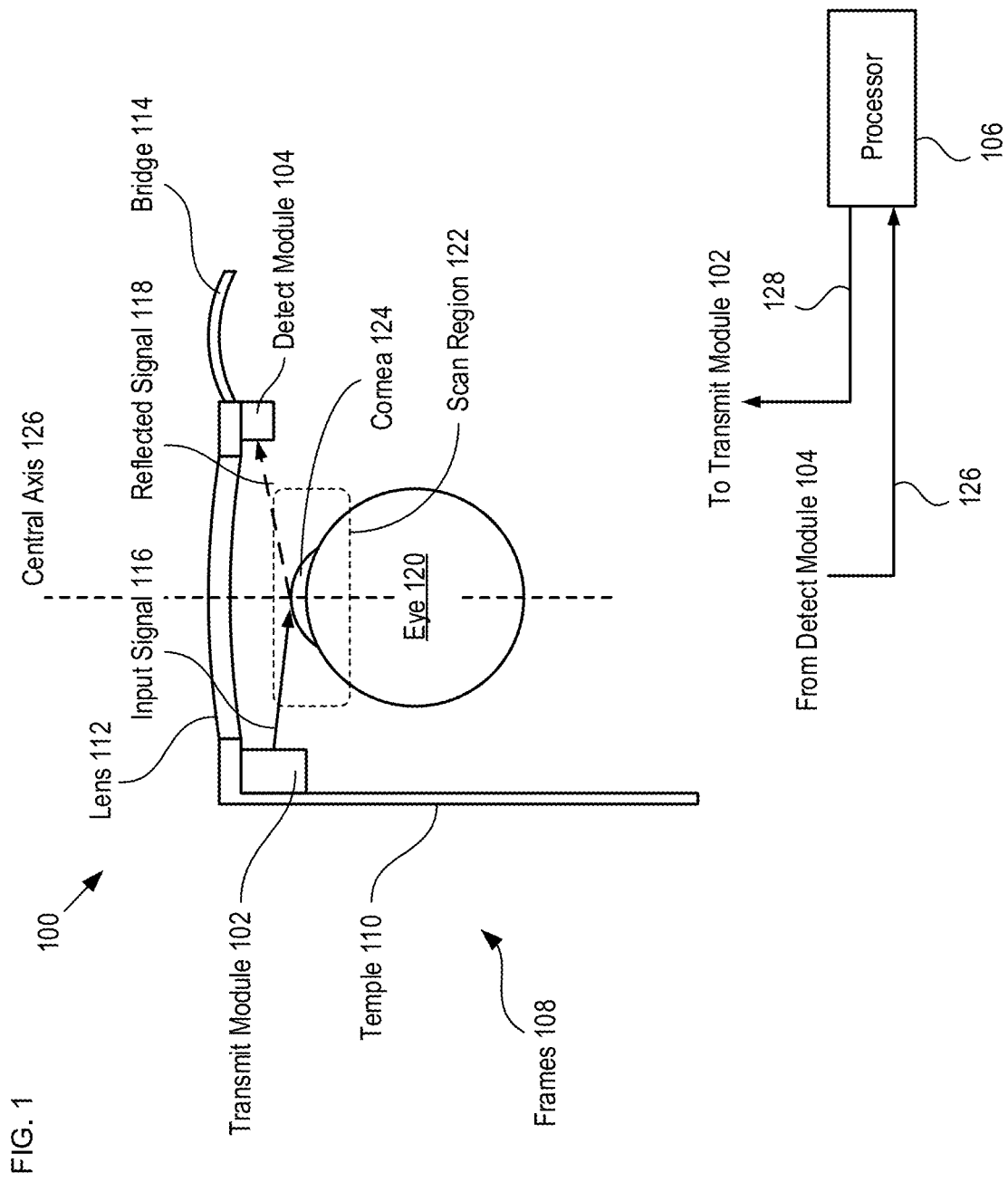
FIG. 1 depicts a schematic drawing of an eye-tracking system in accordance with an illustrative embodiment of the present invention.

FIG. 1 depicts a schematic drawing of an eye-tracking system in accordance with an illustrative embodiment of the present invention. System 100 includes transmit module 102, detect module 104, and processor 106. Transmit module 102 and detect module 104 are arranged on a rigid support in a fixed orientation relative to one eye of a test subject. System 100 enables tracking of a surface feature (e.g., cornea 124) within a two-dimensional region of an eye during typical test subject behavior (e.g., reading, viewing a computer screen, watching television, monitoring a scene, etc.), and estimating the corneal vector of the eye based on the location of the surface feature. For the purposes of this Specification, including the appended claims, the "corneal vector" of an eye is defined as the gaze direction of the eye, which is indicated by a vector extending outward perpendicularly from the center of the pupil of an eye.

Transmit module 102 is a sub-system for providing an optical signal and scanning it in two-dimensions over scan region 122 of eye 120. Transmit module 102 is described in detail below and with respect to FIG. 4.

Detect module 104 is a sub-system for receiving light reflected from scan region 122, providing an electrical signal based on the intensity of the reflected light, and detecting one or more maxima in the electrical signal. Detect module 104 is described in detail below and with respect to FIG. 7.

Processor 106 is a conventional digital processor and controller (e.g., a microcontroller, etc.) operative for controlling transmit module 102, establishing system timing, and estimating the two-dimensional location of cornea 124 within scan region 122. In the depicted example, processor 106 communicates with transmit module 102 and detect module 104 via wired connections (not shown) to transmit and receive control signals 126 and output signal 128. In some embodiments, processor 106 communicates with transmit module 102 and detect module 104 wirelessly. In some embodiments, processor 106 is integrated in one of transmit module 102 and detect module 104.

In the depicted example, system 100 is mounted on eyeglass frames 108, which includes temples 110, lenses 112, and bridge 114. System 100 is mounted on frames 108 such that transmit module 102 and detect module 104 are on opposite sides of central axis 126 of eye 120. Specifically, transmit module 102 is mounted on the frames such that it can scan input signal 116 over the full extent of scan region 122 and detect module 104 is mounted on the frames such that it can receive a portion of input signal 116 reflected from scan region 122 as reflected signal 118.

Figure 2A:
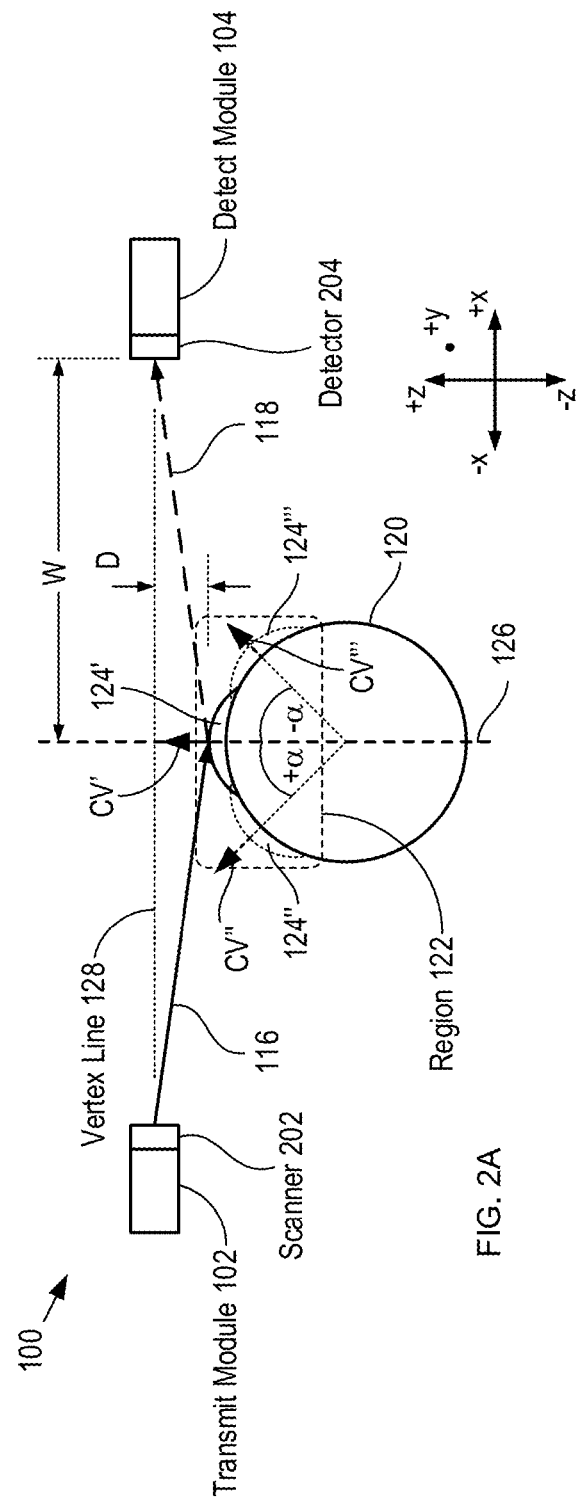
FIG. 2A depicts a schematic drawing of an exemplary geometry for system 100.

FIG. 2A depicts a schematic drawing of an exemplary geometry for system 100.

It is an aspect of the present invention that there exists a configuration of system 100 that gives rise to a unique point on cornea 124 that results in a maximum intensity in the reflection of input signal 116 at detector 204 of detect module 104, where detector 204 is a discrete detector. For the purposes of this Specification, including the appended claims, a "discrete detector" is defined as an optoelectronic device having no more than four electrically independent detection regions on a single substrate, where each detection region is operative for providing one electrical signal whose magnitude is based on the intensity of light incident upon that detection region. Examples of discrete detectors include detectors having only one detection region, split detectors having two detection regions, four-quadrant detectors having four detection regions, and position-sensitive detectors. The definition of discrete detector explicitly excludes individual pixels, or groups of pixels, within array devices for collectively providing spatially correlated image information, such as focal-plane arrays, image sensors, and the like. When input signal 116 is aligned with this point, the angular positions of scanner 202 within transmit module 102 are indicative of the location of this point of maximum reflection within scan region 122, which is indicative of the corneal vector for the eye.

FIG. 2A depicts the position of cornea 124 at three gazing positions: (1) gazing straight ahead and aligned with central axis 126, as indicated by cornea 124' and corneal vector CV'; (2) gazing in the extreme positive direction, as indicated by cornea 124" and corneal vector CV"; and (3) gazing in the extreme negative direction, as indicated by cornea 124'" and corneal vector CV'".

Figure 2B:
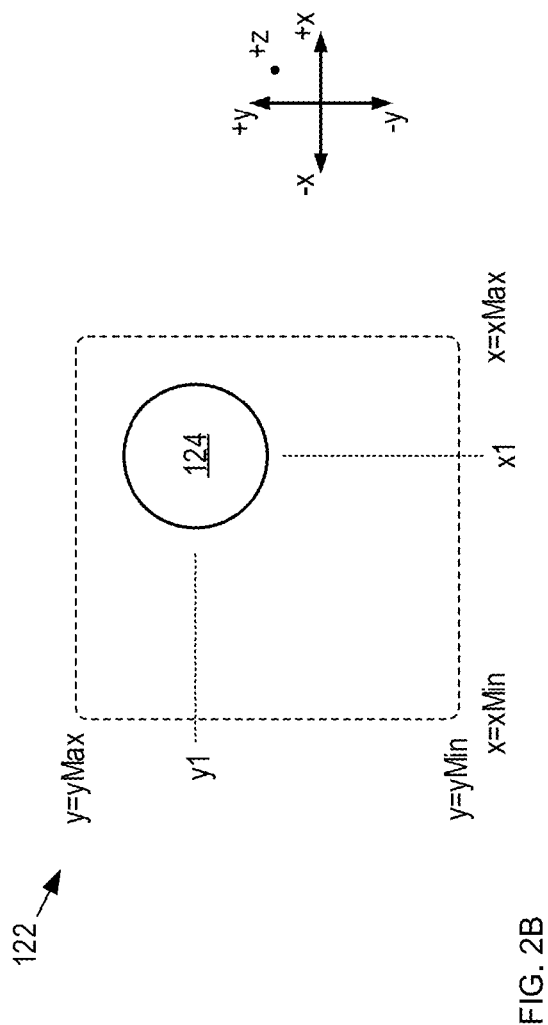
FIG. 2B depicts a schematic drawing of an exemplary scan region 122.

FIG. 2B depicts a schematic drawing of an exemplary scan region 122. Scan region 122 extends from x=xMin to x=xMax and from y=yMin to y=yMax in the x- and y-directions, respectively.

In operation of system 100, scanner 202 sweeps input signal 116 over scan region 122 in two dimensions. When the input signal is incident on cornea 124, reflected signal 118 (i.e., the corneal reflection) sweeps over detector 204. It should be noted that the curvature of the cornea gives rise to a reflective condition that reduces the angle-of-reflection to a narrow range of scanner angles. The position of the scanner that corresponds to the maximum received intensity at the aperture of detector 204 is then used to calculate the location of the cornea, which is then used to estimate corneal vector CV. A more detailed discussion of system 100, its operation, and methods for tracking cornea 124 and estimating corneal vector CV is provided below.

A typical human eye has an eyeball diameter of approximately 24 mm and a cornea having a 9 mm radius of curvature, with the cornea projecting a few millimeters above the eye, thereby defining a surface feature. Based upon this typical eye configuration, in the depicted example, transmit module 102 and detect module 104 are positioned symmetrically about central axis 126 at half-width, W, (half the normal distance across a typical eyeglass lens) of approximately 25 mm. Vertex line 128 is a straight line connecting the center of scanner 202 and the center of the aperture of detector 204. Vertex distance, D, (i.e., the distance between vertex line 128 and the apex of cornea 124 when the eye is aligned with central axis 126) is selected as approximately 14 mm. The locations of transmit module 102 and detect module 104 are selected to substantially maximize the range over which a reflected signal 118 is received for all corneal locations within scan region 122.

As discussed below, an optional calibration procedure can be used to develop a high-resolution relationship between scanner position, reflected beam position, and corneal location relative to a fixed point in space. Such a calibration procedure can also compensate for user-specific variations in system geometry, such as placement of the glasses on the face, corneal shape, etc. Such a calibration procedure is preferably employed in cases where precise control of the absolute gaze direction is desired; however, for many applications, such as those where relative gaze is tracked, calibration is not necessary.

It is another aspect of the present invention that the tracking function of systems in accordance with the present invention relies only on intensity data observed at the fixed position of a discrete detector. As a result, embodiments of the present invention do not require image sensors and image processing algorithms, which are common to most prior-art high-resolution eye-tracking systems. This reduces the power consumption, size, and cost of systems in accordance with the present invention, while simultaneously improving system bandwidth and resolution. Specifically, the resolution of embodiments of the present invention depends on the positioning resolution of the scanning device used, rather than the imaging resolution of a camera or intensity resolution of a position-sensitive detector.

Further, eye tracking using only a single scanned optical signal is faster and consumes less power than the conventional methods, such as video-based eye-tracking. Detection circuits suitable for detecting a single optical signal can also be significantly simpler than the typical image processing circuitry required in conventional, video-based eye-tracking systems. In fact, such detection circuits can often be implemented using conventional CMOS integration. In addition, the use of a discrete detector avoids the need for image processing of a detected image to discern the location of the cornea. As a result, embodiments of the present invention can be much faster than video-based eye-tracking systems of the prior art. Also, conventional video-based eye-tracking systems are bulky and restrictive for the user due to the size and complexity of their required image sensors and processing systems. In contrast, embodiments of the present invention can be simple and compact and, therefore, more unobtrusive to the user.

It should be noted that system 100 has better performance when cornea 124 is rotated toward transmit module 102 relative to central axis 126 (i.e., □ is positive, as indicated in FIG. 2A) than when the cornea is rotated away from the transmit module (i.e., □ is negative). This is due to purely geometric considerations, since a given change in mirror position gives rise to a greater change in the angle at which reflected signal 118 reflects when □ is positive than when it is negative, and also since the angle of incidence onto the curved surface of the cornea is more shallow when the cornea is pointing towards the detector. As a result, in some embodiments, transmit and detect modules are located on both sides of eye 120 to provide high-resolution tracking over the entire width of scan region 122. In other words, two systems 100 (typically, with a single processor 106) are located on frames 108 but oriented in opposite directions.

In some embodiments, location sensitivity is improved by one or more of:
    i. increasing vertex distance, D; or
    ii. reducing half-width, W; or
    iii. using a second system 100 to track the other eye of the subject; or
    iv. limiting the size of scan region 122; or
    v. any combination of i, ii, iii, and iv.

It is yet another aspect of the present invention that the resolution criterion for determining the location of cornea 124 does not impose stringent constraints on the quality of the spot that is incident on the detector of detect module 104. As discussed below, detect module 104 includes a photodetector that provides an electrical signal that represents the average optical power incident upon its aperture. This can be written as a two dimensional integral of power over the surface area of the detector (at any position of the incidence beam). As the beam sweeps the surface, the output of the detector may be calculated by an integral of the beam profile in the vertical direction, followed by a convolution integral. It should be noted that these two integrals are decoupled and therefore the profile of the beam is first integrated in the vertical direction and then the convolution-like integral is evaluated:

$$(p*g)(\theta) = \int_{-\infty}^{\infty} p(\theta)g(\theta-v)dv. \qquad (1)$$

In Equation 1, the angular position, v, of scanner 202 shifts the spot g(□) over the aperture p(□) of detector 204 to perform convolution in cylindrical coordinates. The integral is solved by multiplication in the (spatial) Fourier domain, which also shows that detector 204 performs spatial filtering on reflected signal 118. As a result, in order for system 100 to uniquely identify the location of cornea 124 that results in maximum reflection, the only requirement on the beam profile of input signal 116 is that it gives rise to a far-field pattern having a region of global maximum intensity.

Figure 3A:
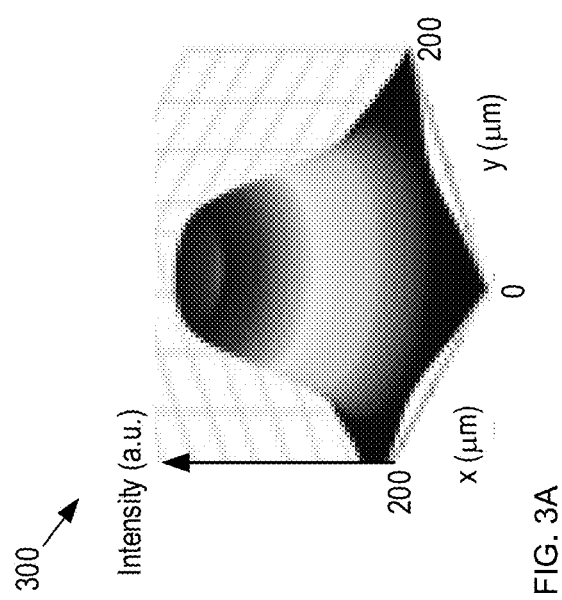
FIG. 3A depicts an example of a beam profile suitable for use in the present invention.

FIG. 3A depicts an example of a beam profile suitable for use in the present invention. Beam profile 300 is representative of the beam profile of a low-cost vertical-cavity surface-emitting laser (VCSEL) and is characterized as a substantially circular beam having a "donut-shaped" intensity profile. In some embodiments, beam profile 300 has a beam profile other than that of a donut.

Figure 3B:
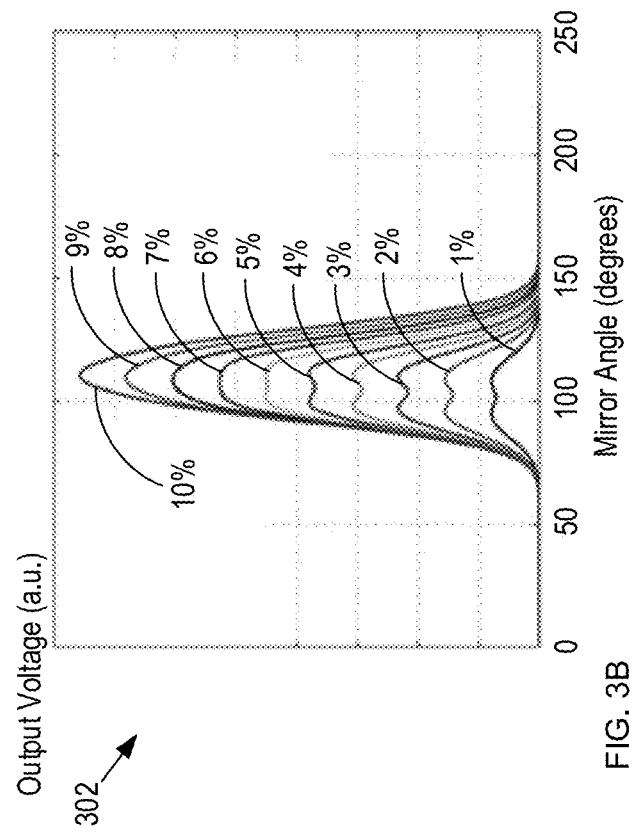
FIG. 3B depicts a plot of the amplitude of the electrical signal output by detector 204 as a function of mirror angle and percentage of the beam waist of reflected signal 118 occupied by the aperture of detector 204.

FIG. 3B depicts a plot of the amplitude of the electrical signal output by detector 204 as a function of mirror angle and percentage of the beam waist of reflected signal 118 occupied by the aperture of detector 204. Plot 302 includes traces that correspond to percentages of beam waist occupied by the aperture of detector 204 ranging from 1% to 10%, as indicated. It can be seen from plot 302 that, as long as detector 204 has a sufficiently large aperture, its output signal will include a single amplitude peak. In the depicted example, the spatial filtering provided by detector 204 leads to the removal of any spatial irregularity in the detected beam waist when the aperture of detector 204 occupies only 7% of the beam waist of reflected signal 118. In some embodiments, detector 204 includes a focusing lens for increasing its effective aperture.

It should be noted that, typically, the spatial frequencies of the irregularities in the beam profile of even a low-cost VCSEL are high enough to allow the use of a detector having a relatively small aperture, such as a surface-mount photodetector.

Figure 4:
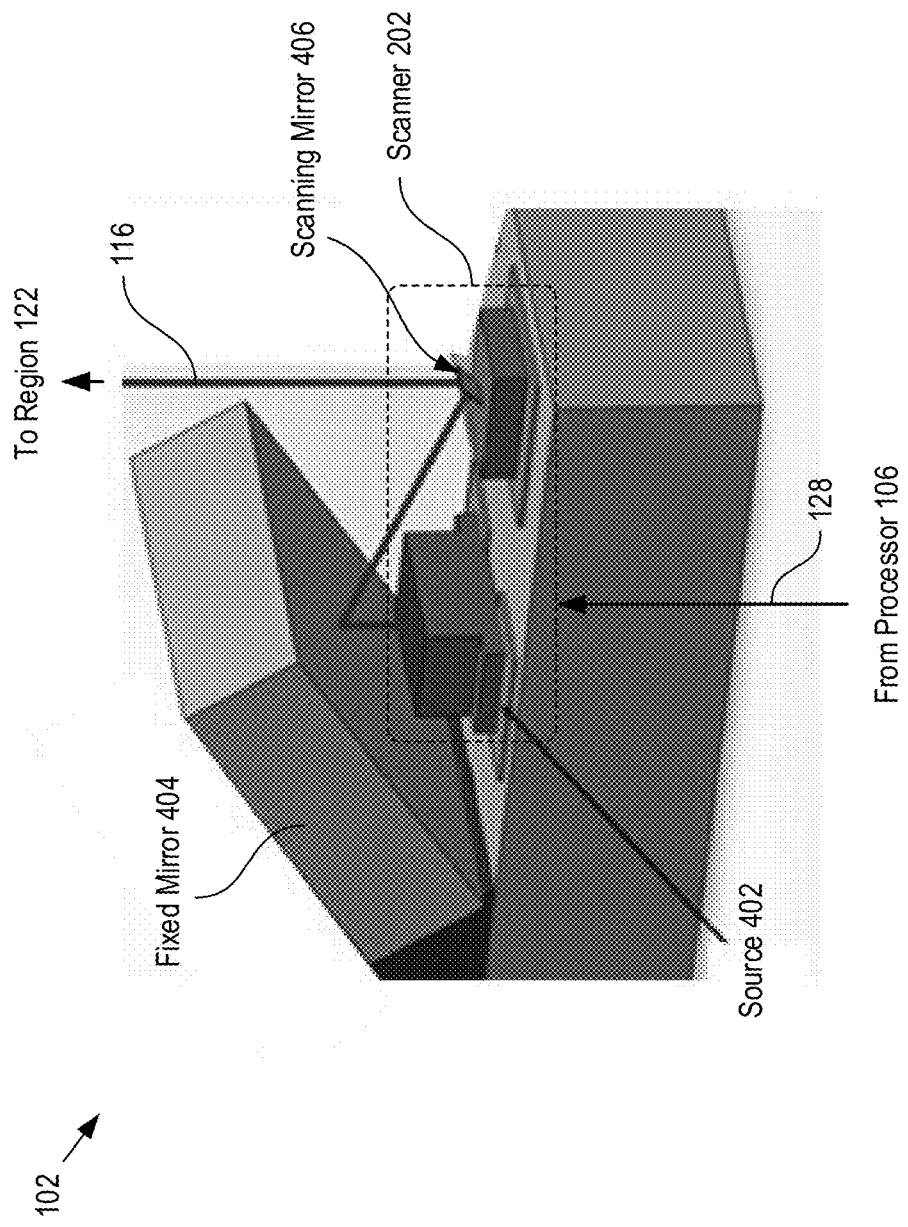
FIG. 4 depicts a schematic drawing of a perspective view of a transmit module in accordance with the illustrative embodiment.

FIG. 4 depicts a schematic drawing of a perspective view of a transmit module in accordance with the illustrative embodiment. Transmit module 102 includes scanner 202, which comprises source 402, fixed mirror 404, and scanning mirror 406. Scanner 102 is operative for scanning input signal 116 in two dimensions to interrogate the entirety of scan region 122. In some embodiments, transmit module 102 does not interrogate the entirety of scan region 122.

Source 402 is a conventional VCSEL that is operatively coupled with suitable drive circuitry (not shown). Source 402 generates input signal 116 in response to command signal 128 from processor 106. As discussed above, input signal 116 is preferably characterized by a beam profile that gives rise to a far-field pattern having a global intensity maximum. In some embodiments, source 402 is modulated to reduce power consumption. Modulation of source 402 also enables the signal-to-noise ratio (SNR) of system 100 to be increased.

Fixed mirror 404 is a conventional first-surface reflector suitable for reflecting the light output by source 402 toward scanning mirror 406 without significant loss. Fixed mirror 404 may be used to align the optical path in a manufacturing process.

Scanning mirror 406 is a two-dimensional MEMS-based scanning mirror that is arranged to receive the light reflected toward it by fixed mirror 404 and scan the light over scan region 122 as input signal 116.

In some cases, scanning mirror 406 is characterized by a curvature that arises due to material stresses and features, such as etch release holes. In some embodiments, this curvature is exploited by controlling the total path length between the emitting facet of source 402 and the reflecting surface of scanning mirror 406 such that the curvature of the mirror compensates for the divergence of the light beam emitted from the VCSEL.

Figure 5A:
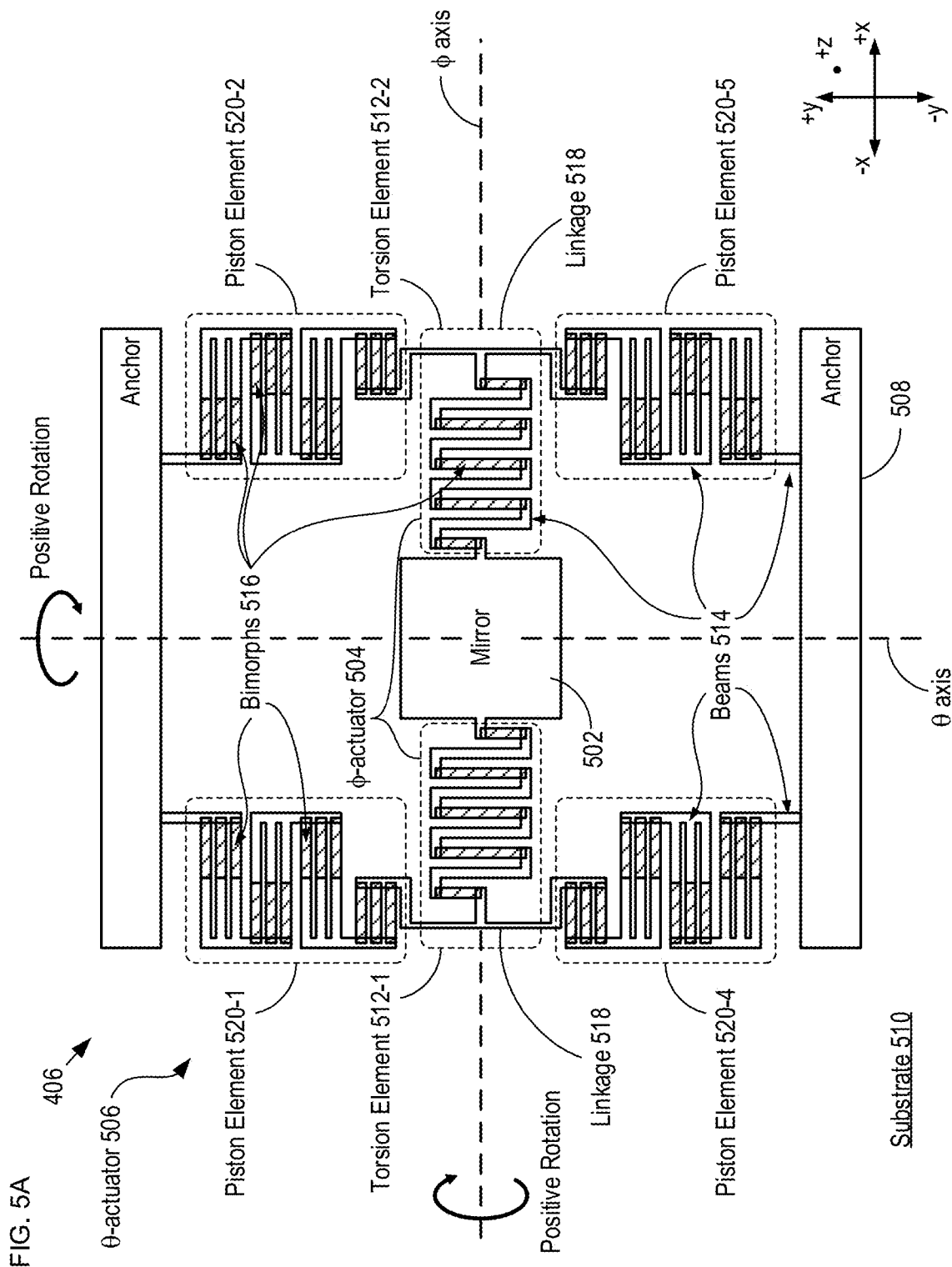
FIG. 5A depicts a schematic drawing of a scanning mirror in accordance with the illustrative embodiment.

FIG. 5A depicts a schematic drawing of a scanning mirror in accordance with the illustrative embodiment. Scanning mirror 406 includes mirror 502, □-actuator 504, □-actuator 506, and anchor 508, which are disposed on substrate 510. Scanning mirror 206 is a MEMS-based, two-dimensional scanning mirror suitable for fabrication via planar processing techniques. Preferably, scanning mirror 406 is suitable for fabrication in a conventional CMOS foundry. Actuators suitable for use in scanning mirror 406, as well as methods suitable for forming them, are described in U.S. Patent Publication 20150047078, entitled "Scanning Probe Microscope Comprising an Isothermal Actuator," published Feb. 12, 2015, and U.S. Patent Publication 20070001248, entitled "MEMS Device Having Compact Actuator," published Jan. 4, 2007, each of which is incorporated herein by reference.

Mirror 502 is a substantially square plate of single-crystal silicon that is operative as a first-surface reflector for input signal 116. In some embodiments, mirror 502 includes a surface layer of a highly reflective material, such as gold, to enhance its reflectivity. Mirror 502 is movable relative to substrate 510 and operatively coupled with each of □-actuator 504 and □-actuator 506. In some embodiments, mirror 502 comprises a different material suitable for use as a MEMS structural material, such as polysilicon, silicon carbide, silicon-germanium, a III-V semiconductor, a II-VI semiconductor, a composite material, and the like. In some embodiments, mirror 502 has a shape other than square, such as circular, elliptical, irregular, etc.

It is an aspect of the present invention that the use of electro-thermo-mechanical actuators to control the position of mirror 502 about its rotation axes affords embodiments of the present invention with significant benefits, including:
 i. CMOS-compatible operating voltage (3.3V); or
 ii. small footprint (present embodiment 700 □m×700 □□m); or
 iii. large angular deflection (>45 degrees mechanical in 2 DOF); or
 iv. low power (<10 mW); or
 v. high speed (≥5-kHz resonance); or
 vi. low cost; or
 vii. any combination of i, ii, iii, iv, v, and vi.

As a result, embodiments of the present invention preferably employ electro-thermo-mechanical actuators for each of □-actuator 504 and □-actuator 506. It is also preferred that each of □-actuator 504 and □-actuator 506 is an isothermal actuator since isothermal actuation mitigates parasitic effects that arise from thermal coupling between axes of rotation. For the purposes of this Specification, including the appended claims, "isothermal operation" is defined as operation at a constant power dissipation throughout an operating range. A device or system that operates in isothermal fashion dissipates constant power over its operating range, which results in a steady-state heat flow into and out of the device or system. For example, an isothermal actuator is an actuator that operates at a constant power throughout its operating range. In some cases, an isothermal actuator includes a plurality of actuating elements where at least one of the actuating elements operations in non-isothermal fashion; however, the plurality of actuating elements are arranged such that they collectively operate in isothermal fashion.

☐-actuator 504 is an isothermal torsional actuator operative for rotating plate 502 about the ☐-axis, which is substantially aligned with the x-axis in the depicted example. ☐-actuator 504 includes torsion elements 512-1 and 512-2, each of which is mechanically coupled between mirror 502 and anchors 508 by beams 514. Beams 514 are rigid linkages comprising the same structural material as mirror 502 (i.e., single-crystal silicon).

Each of torsion elements 512-1 and 512-2 includes a plurality of bimorphs 516, which are grouped into operative sets. Adjacent operative sets are rigidly interconnected via beams 514 such that bending of the operative sets within a torsion element is additive. For clarity, elements comprising structural material (e.g., the material of mirror 502, anchors 508, and beams 514) is depicted without cross-hatching, while bimorph elements 516 are depicted with cross-hatching.

Torsion elements 512-1 and 512-2 are rigidly connected rigid linkages 518 and arranged such that they rotate about the ☐-axis in the same direction when subjected to opposite temperature changes. As a result, their collective power dissipation remains constant during operation. The temperature of torsion elements 512-1 and 512-2 is controlled via controlling electrical power dissipation (i.e., ohmic heating) in the elements themselves. In some embodiments, the temperature of the bimorphs in the torsional elements is controlled by controlling power dissipation in ohmic heaters disposed on the elements. In some embodiments, a heat source external to the torsion elements is used to control their temperature, such as heater elements disposed on the surface of substrate 510.

☐-actuator 506 is an isothermal piston actuator operative for rotating plate 502 about the ☐-axis, which is substantially aligned with the y-axis in the depicted example. ☐-actuator 506 comprises piston elements 520-1 through 520-4 (referred to, collectively, as piston elements 520) which are arranged in isothermal pairs. ☐-actuator 506 is mechanically coupled between linkages 518 and anchors 508 by a set of beams 514. Each of piston elements 520 includes a plurality of beams 514 and bimorphs 516, which are arranged to give rise to vertical actuation in response to a temperature change. The temperature of piston elements 520 is controlled as described above and with respect to torsional elements 512.

Upon their release from substrate 510, piston elements 520 collectively move mirror 502 in the positive z-direction (i.e., away from the substrate surface). Each of the piston elements is designed such that an increase in its power dissipation gives rise to its contraction, thereby moving its connection to mirror 502 toward the substrate. Piston elements 520 are arranged in isothermal pairs—piston elements 520-1 and 520-2 and piston elements 520-5 and 520-4. As a result, an increase in the power dissipated in piston elements 520-2 and 520-5 and a commensurate decrease in the power dissipated in piston elements 520-1 and 520-4 induces positive (as indicated) rotation of mirror 502 about the ☐-axis while maintaining a constant power dissipation in ☐-actuator 506 overall. In similar fashion, by decreasing the power dissipated in piston elements 520-2 and 520-5 and increasing the power dissipated in piston elements 520-1 and 520-4 by the same amount, a negative rotation of mirror 502 about the ☐-axis is induced while the power dissipated in ☐-actuator 506 remains constant.

It should be noted that the actuator and mirror configuration of scanning mirror 406 is one of many possible MEMS-based scanning mirror configurations within the scope of the present invention. Some alternative embodiments in accordance with the present invention include a ☐-actuator and/or ☐-actuator that is actuated by another actuation means, such as electrostatic, electromagnetic, magnetostrictive, piezoelectric, and the like. Some alternative embodiments in accordance with the present invention include an ☐-actuator and/or ☐-actuator that is non-isothermal. Some alternative embodiments in accordance with the present invention include a movable mirror that includes an optical element, such as one or more diffractive lenses (e.g., a one- or two-dimensional Fresnel lens, a holographic lens, etc.), one or more refractive lenses, an active optical source, one or more diffraction gratings, one or more prisms, and the like.

Figure 5B:
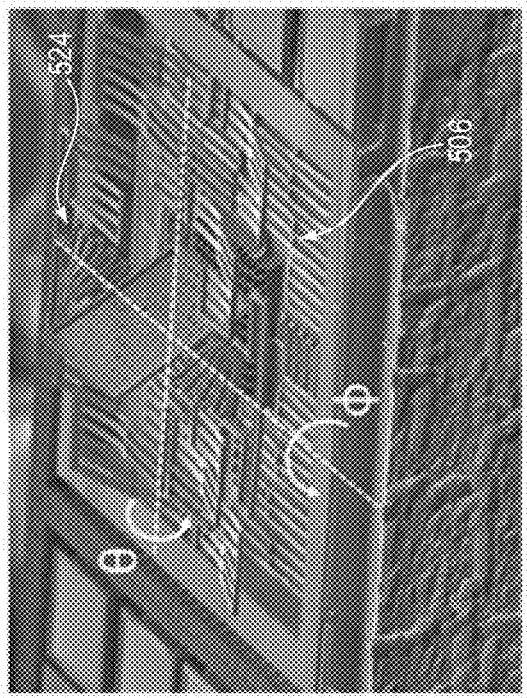
FIG. 5B depicts a photograph of a scanning mirror analogous to scanning mirror 406.

FIG. 5B depicts a photograph of a scanning mirror analogous to scanning mirror 406; however, scanning mirror 522 includes a non-isothermal torsional actuator, actuator 524, for rotation about the ☐-axis and an isothermal piston actuator 506 for rotation about the ☐-axis, as indicated.

Figure 5C:
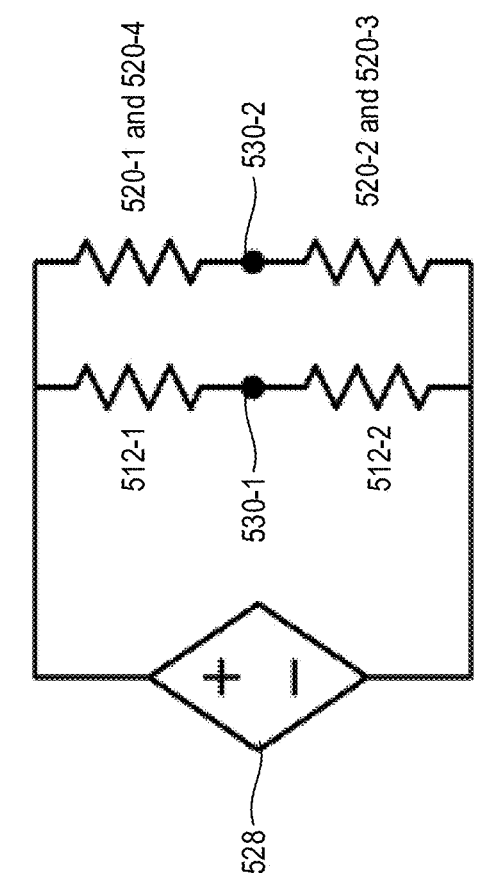
FIG. 5C depicts an electrical arrangement suitable for driving a scanning mirror that employs isothermal actuators for each axis of rotation.

FIG. 5C depicts an electrical arrangement suitable for driving a scanning mirror that employs isothermal actuators for each axis of rotation. Circuit 526 includes source 528 and terminals 530-1 and 530-2. Terminal 530-1 receives an ☐-axis control signal from processor 106 that alters the current flow through torsion elements 512-1 and 512-2, thereby determining their relative power dissipation. In similar fashion, terminal 530-2 receives a ☐-axis control signal from processor 106 that alters the current flow through piston elements 520-1 through 520-4, thereby determining their relative power dissipation.

The arrangement of circuit 526 reduces the number of drive signals required in control signal 128 by a factor of 2, thereby reducing the cost and complexity of the drive electronics included in transmit module 102.

It should be noted that, preferably, PWM signals are used at terminals 530-1 and 530-2. The use of PWM signals enables linear control of the power dissipated by the resistance of each electro-thermo-mechanical element while the overall power dissipated in each axis remains constant.

FIGS. 6A-D depict photographs of alternative MEMS-based scanning mirrors in accordance with the present invention. Mirrors 600, 606, 612, and 618 show a variety of different combinations of actuators and optical-element-containing mirrors. It will be clear to one skilled in the art, after reading this Specification, however, that mirrors 600, 606, 612, and 618 represent merely a few of the possible mirror and actuator combinations within the scope of the present invention.

Figure 6A:
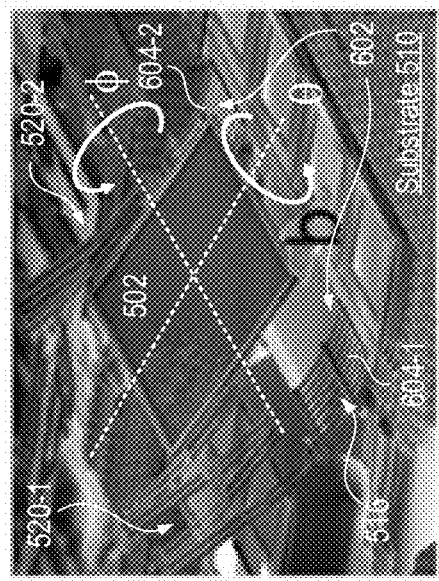
FIGS. 6A-D depict photographs of alternative MEMS-based scanning mirrors in accordance with the present invention.

FIG. 6A depicts a photograph of an alternative scanning mirror in accordance with the present invention. Scanning mirror 600 includes mirror 502, isothermal piston actuators 520-1 and 520-2 for mirror rotation about the ☐-axis, and non-isothermal resonant bimorph actuator 602 for inducing mirror rotation about the ☐-axis.

Bimorph actuator 602 includes vertical actuators 604-1 and 604-2. Each vertical actuator includes a set of bimorphs 516, which are arranged to bend away from substrate 510 upon their release during MEMS fabrication. During operation, bimorphs 516 bend downward (toward substrate 510) in response to an increase in their temperature and upward in response to a decrease in temperature. By applying a signal at the natural frequency of the device, the first resonant mode causes actuators 604-1 and 604-2 to rotate the mirror 502 about the ☐☐ axis. The isothermal nature of the ☐☐ axis actuator ensures that coupling between the orthogonal axes is suppressed.

Figure 6B:
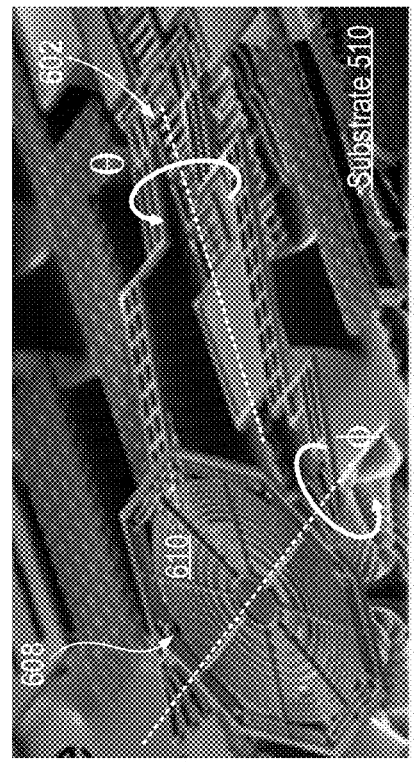

FIG. 6B depicts a photograph of another alternative scanning mirror in accordance with the present invention. Scanning mirror 606 is analogous to scanning mirror 600; however, scanning mirror 606 includes circular mirror 608, which includes integrated optical element 610. In the depicted example, optical element 610 is a Fresnel lens for forming a substantially circular spot on eye 120; however, one skilled in the art will recognize, after reading this Specification, that optical element 610 can include any conventional diffractive or refractive element suitable for fabrication in, or disposition on, mirror 608 (or any mirror in accordance with the present invention). Optical elements suitable for use in embodiments of the present invention include, without limitation, refractive lenses, diffractive lenses, holographic lenses, and the like.

Figure 6C:
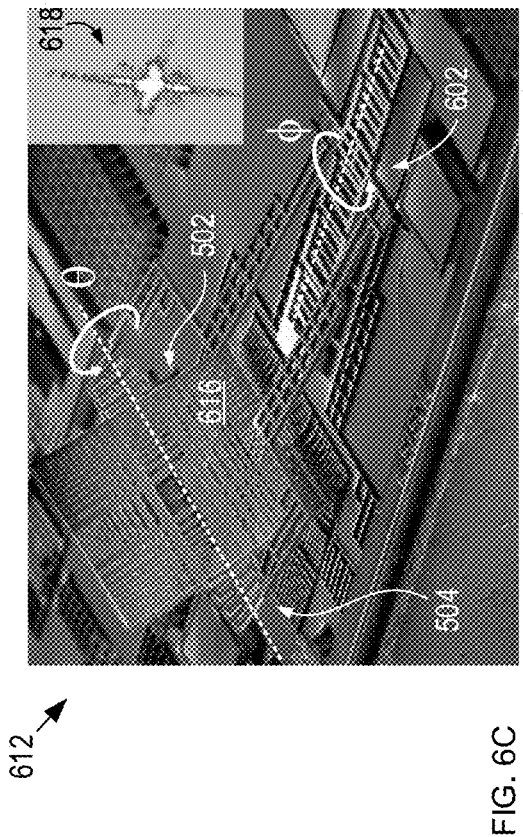

FIG. 6C depicts a photograph of another alternative scanning mirror in accordance with the present invention. Scanning mirror 612 is analogous to scanning mirror 600; however, scanning mirror 612 includes optical element 616, which is integrated into the surface of mirror 502.

In the depicted example, optical element 616 includes a pair of cylindrical Fresnel lenses that are arranged orthogonally and formed in the body of mirror 502. As a result, mirror 502 forms input signal 116 into a cross-shaped light pattern on scan region 122. The use of an input signal that forms a cross pattern on the eye can advantageously improve the robustness of tracking algorithms used to track the location of cornea 124 within scan region 122. An exemplary cross-shaped light pattern 618, formed by optical element 616, is depicted in the inset in the upper right corner of FIG. 6C.

Figure 6D:
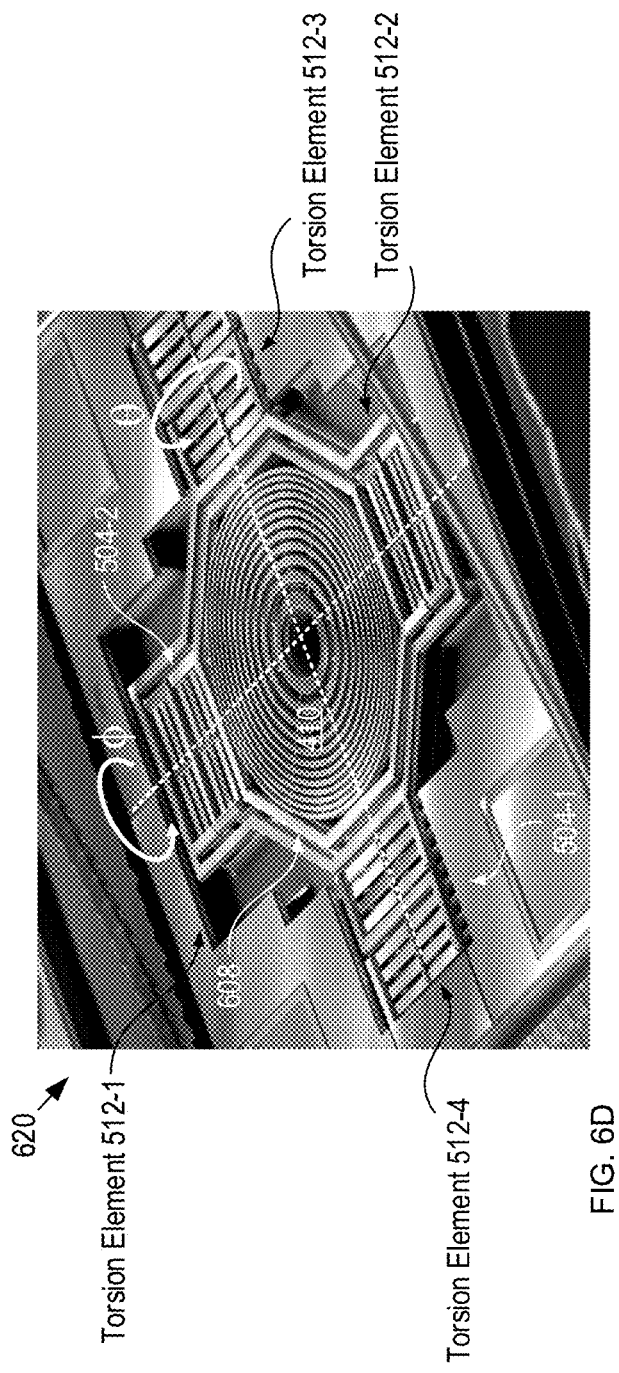

FIG. 6D depicts a photograph of yet another alternative scanning mirror in accordance with the present invention. Scanning mirror 620 is analogous to scanning mirror 606; however, scanning mirror 620 includes isothermal torsional actuators 504-1 and 504-2 for rotating mirror 608 about the ☐- and ☐-axes, respectively.

Embodiments of the present invention preferably employ electro-thermo-mechanical actuators, such as those described above, to control the position of mirror 502 about its rotation axes. Such actuators offer unparalleled positioning accuracy and repeatability in response to applied drive signals. As a result, they can be operated in open-loop fashion without incurring significant positioning inaccuracy. In addition, by employing structural material that remains in a linear stress-strain configuration throughout the operating range of the actuator, little or no drift in position response arises over time. In some embodiments, however, sensors (e.g., piezoresistive strain sensors, capacitive sensors, optical sensors, etc.) are included in the scanning mirror to further improve positioning accuracy. Further, in some embodiments, a pulse-width modulation (PWM) drive scheme is employed to control the position of the scanning mirror, as discussed below.

In some embodiments, piezoresistive strain sensors are included in the beams of the thermal actuators to enable the devices to be placed in resonance so as to maintain constant phase and amplitude over a wide range of operating conditions.

In some embodiments, scanning mirror 406 is another scanning element suitable for scanning input signal 116 over scan region 122. Scanning elements suitable for use in the present invention include, without limitation, scanning prisms, Risley prisms, tunable diffraction gratings, variable blazed gratings, coupled pairs of single-axis scanning mirrors, non-MEMS-based scanning mirrors, electro-optic beam scanners, galvanometer mirrors, and the like.

In some embodiments, the output of source 402 is provided directly to scanning mirror 406. In some embodiments, source 402 is optically coupled with scanning mirror 406 via a waveguide such as an optical fiber, planar-lightwave circuit waveguide, and the like.

In some embodiments, transmit module 102 includes a scanner wherein the orientation of source 402, itself, is scanned in one or two dimensions relative to scan region 122. In other words, such a scanner combines the operations of both source 402 and scanning mirror 406 in a single integrated device. For example, in some embodiments, an active light source is integrated directly onto the surface of scanning mirror 406 via hybrid and/or monolithic integration techniques. Monolithic integration techniques suitable for integrating an active light source on scanning mirror 406 include, for example, those described by Liang, et al., in "Hybrid Integrated Platforms for Silicon Photonics," *Materials*, Vol. 3, pp. 1782-1802 (2010), which is incorporated herein by reference.

Figure 7:
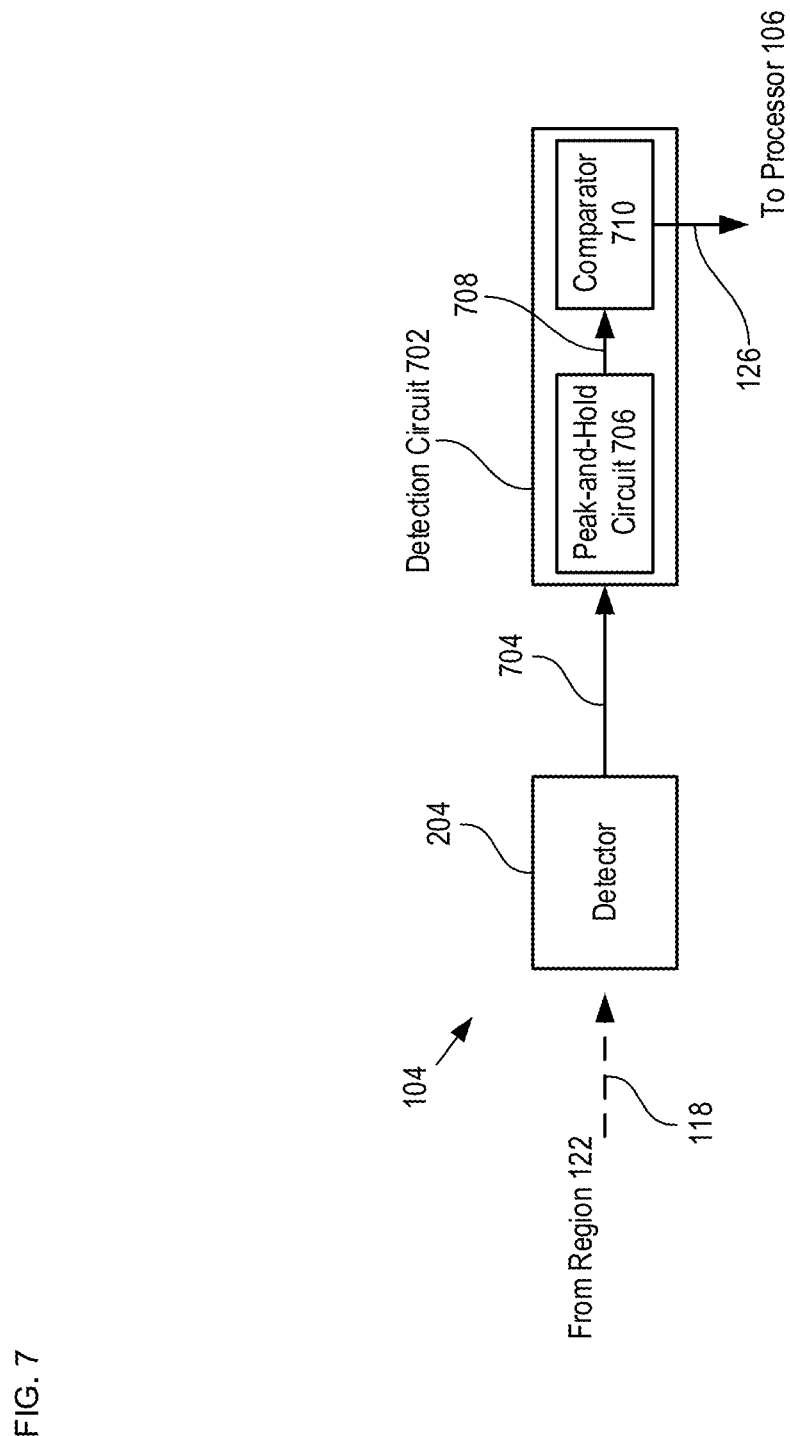
FIG. 7 depicts a schematic drawing of a detect module in accordance with the illustrative embodiment.

Returning now to the illustrative embodiment, FIG. 7 depicts a schematic drawing of a detect module in accordance with the illustrative embodiment. Detect module 104 includes detector 204 and detection circuit 702.

As discussed above, detector 204 is a conventional, single-detection-region photodetector for receiving reflected signal 118 and providing a single electrical signal, electrical signal 704, such that the magnitude of electrical signal 704 is based on the intensity of reflected signal 118. Detector 204 has sensitivity and detection bandwidth sufficient to enable eye tracking at a rate dictated by the application for which system 100 is intended. Typically, detector 204 enables operating rates within the range of a few Hz to tens of kHz. Detector 204 has a detection surface that is large enough to accommodate the full beam profile of reflected signal 118 such that detector 204 can provide an output that represents the average power of the light incident upon it. Typically, detector 204 has a substantially square detection surface that is tens to hundreds of microns on a side. In the depicted example, detector 204 is a photodetector having a square detection region of 500 microns on a side. In some embodiments, detector 204 includes a filter for blocking ambient light from reaching its aperture. In some embodiments, detector 204 includes a focusing lens for increasing the effective aperture of the photodetector. One skilled in the art will recognize, after reading this Specification, that detector 204 can include any optoelectronic device operative for converting an optical signal into an electrical signal, wherein the magnitude of the electrical signal is based on the intensity of the light signal.

Detection circuit 702 is an integrated circuit operative for identifying peaks in electrical signal 704 and providing output signal 126 to processor 106. In the depicted example, detection circuit 702 includes a peak-and-hold circuit 706 to set a threshold value for a comparator 710, which collectively convert eye position into a time-domain signal that is readily captured by processor 106. The operation of detection circuit 702 is described in detail below and with respect to FIGS. 9 and 10. One skilled in the art will recognize, after reading this Specification, that myriad alternative detection circuits are within the scope of the present invention.

In some embodiments, detector 204 is a discrete detector that includes more than one detection region and, therefore, provides more than one electrical output signal. In such embodiments, detection circuit 702 is operative for determining the relative magnitudes of the plurality of electrical signals. These relative magnitudes can then be used to estimate an offset of the position at which a reflection maximum is detected during a scan of input signal 116 through scan region 122 from the location of the global reflection maximum within the complete area of scan region 122. As a result, the paths of subsequent scans can be adjusted to more quickly intersect the location of the global maximum and identify the location of cornea 124 and corneal vector CV.

It should be noted that, within the scope of the present invention, there are numerous approaches for scanning input signal within scan region 122 that are effective for identifying the two-dimensional location of a surface feature within scan region 122. Several non-limiting examples are provided herein.

Figure 8:
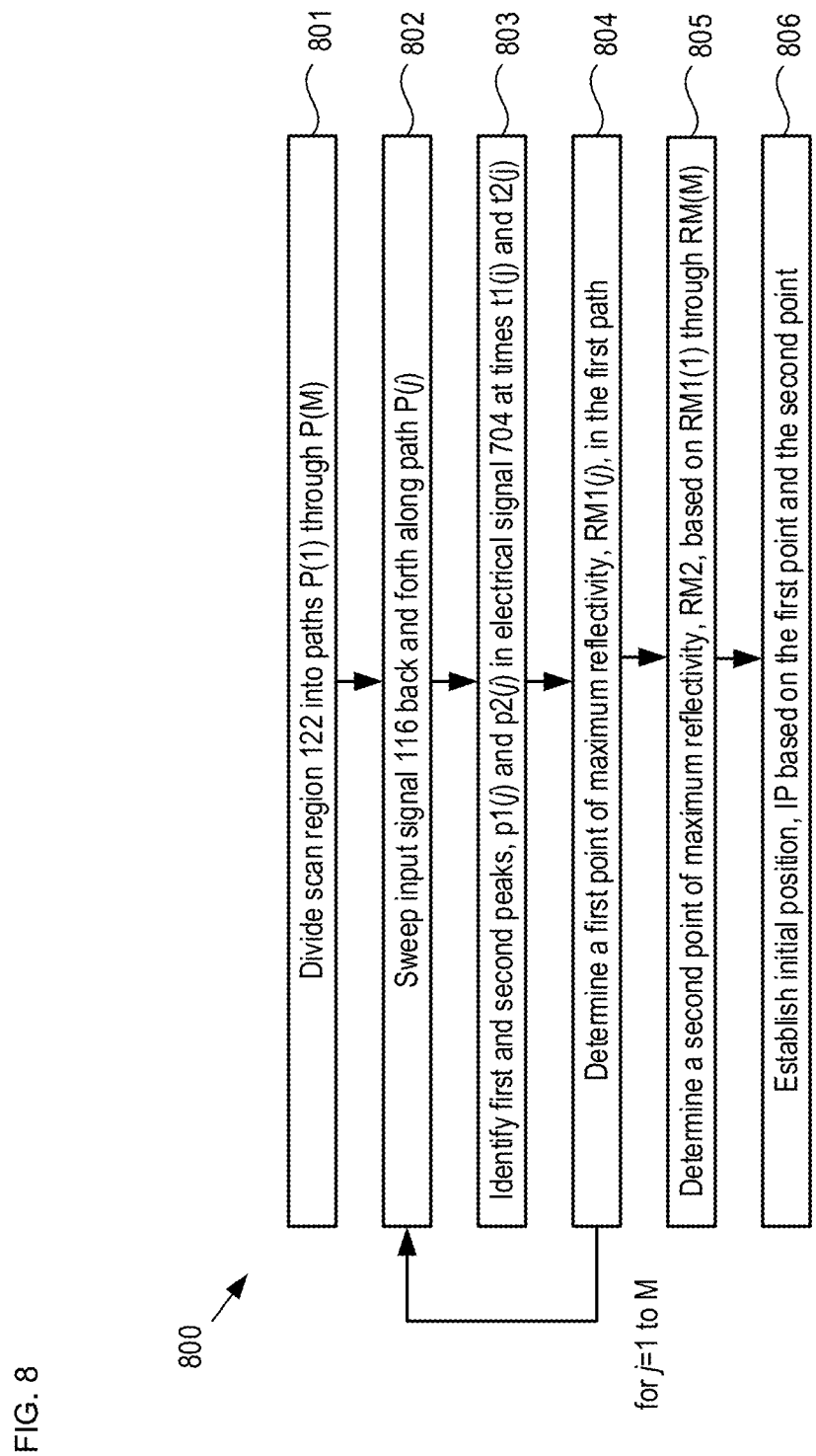
FIG. 8 depicts an initialization procedure for approximating the location of a surface feature on an eye.

FIG. 8 depicts an initialization procedure for approximating the location of a surface feature on an eye. Method 800 is typically performed prior to any of the high-resolution eye tracking methods described below in order to establish an initial point, IP, at which the subsequent higher-resolution method should begin. Method 800 begins with operation 801, wherein scan region 122 is divided into an array of M paths, P(1) through P(M), each of which traverses the scan region along a first direction, and where the paths are equally arranged along a second direction that is orthogonal to the first direction. In the depicted example, M=8 and each path, P(j), where i=1 through 8, is aligned with the x-direction. The 8 paths are equally spaced along the y-direction from y=yMin to yMax. It should be noted that the value of M, as well as the spacing between the paths, is a matter of design choice and is typically based upon the size of input signal 116, the size of scan region 122, and the desired operating rate of system 100.

For j=1 through M:

At operation 802, input signal 116 is swept back and forth along path, P(i).

At operation 803, first and second peaks, p1(j) and p2(j) in electrical signal 704 are identified, as are times t1(j) and t2(j) at which they are detected.

At operation 804, a first point of maximum reflectivity, RM(j) in path P(j) is determined based on times t1(j) and t2(j).

At operation 805, a second point of maximum reflectivity along the y-direction is established based on the magnitudes of p1(1) through pl(8). In some embodiments, the second point is established as the y-position of the path having the largest peak. In some embodiments, the second point is based on the complete set of the magnitudes of peaks p1(1) through p1(8) using, for example, interpolation, etc.

At operation 806, the initial position, IP, is established based on the first and second points.

Method 800 is preferably performed prior to employing subsequent higher-resolution eye-tracking methods in accordance with the present invention (examples of which are described below); however, in some embodiments, natural eye movement and motion of scanner 202 due to electrical noise is relied upon to give rise to sufficient intersection of input beam and cornea 124 to establish the initial position.

As mentioned briefly above, in applications where high-resolution absolute eye tracking is desired, an optional calibration routine can be performed after the initialization procedure outlined above. Calibration improves the accuracy of the relationship between the mirror 502 about the □- and □-axes and the direction of the user's gaze (i.e., corneal vector, CV). In a typical calibration procedure, the test subject is instructed to look at a plurality of distinct points (e.g. nine) on a screen. The position of mirror 502 that corresponds to the peak intensity at each point is then measured. A coordinate transformation between the measured positions to the actual positions is calculated. This coordinate transformation is then applied to subsequent eye-tracking measurements. It should be noted that system 100 remains calibrated even after removal of the screen as long as the relative positions of scanner 202, detector 204, and eye 120 remain fixed.

An alternative calibration procedure that requires significantly less computation can also be used in many instances. In this alternative procedure, the test subject presses a "grab" button while looking at an arbitrary point on the screen. The point measured by the eye-tracking system is then displayed on the screen. Typically, initially, the measured point is slightly offset from the point at which the user is looking. While the grab button is pressed, the test subject redirects their gaze at the projected point. Upon release of the grab button, the offset between the two points at which the test subject's eye had been directed is calculated and the difference is subtracted from the measured value. Repeated performance of this alternative calibration procedure results in additional improvement in the calibration.

Figure 9:
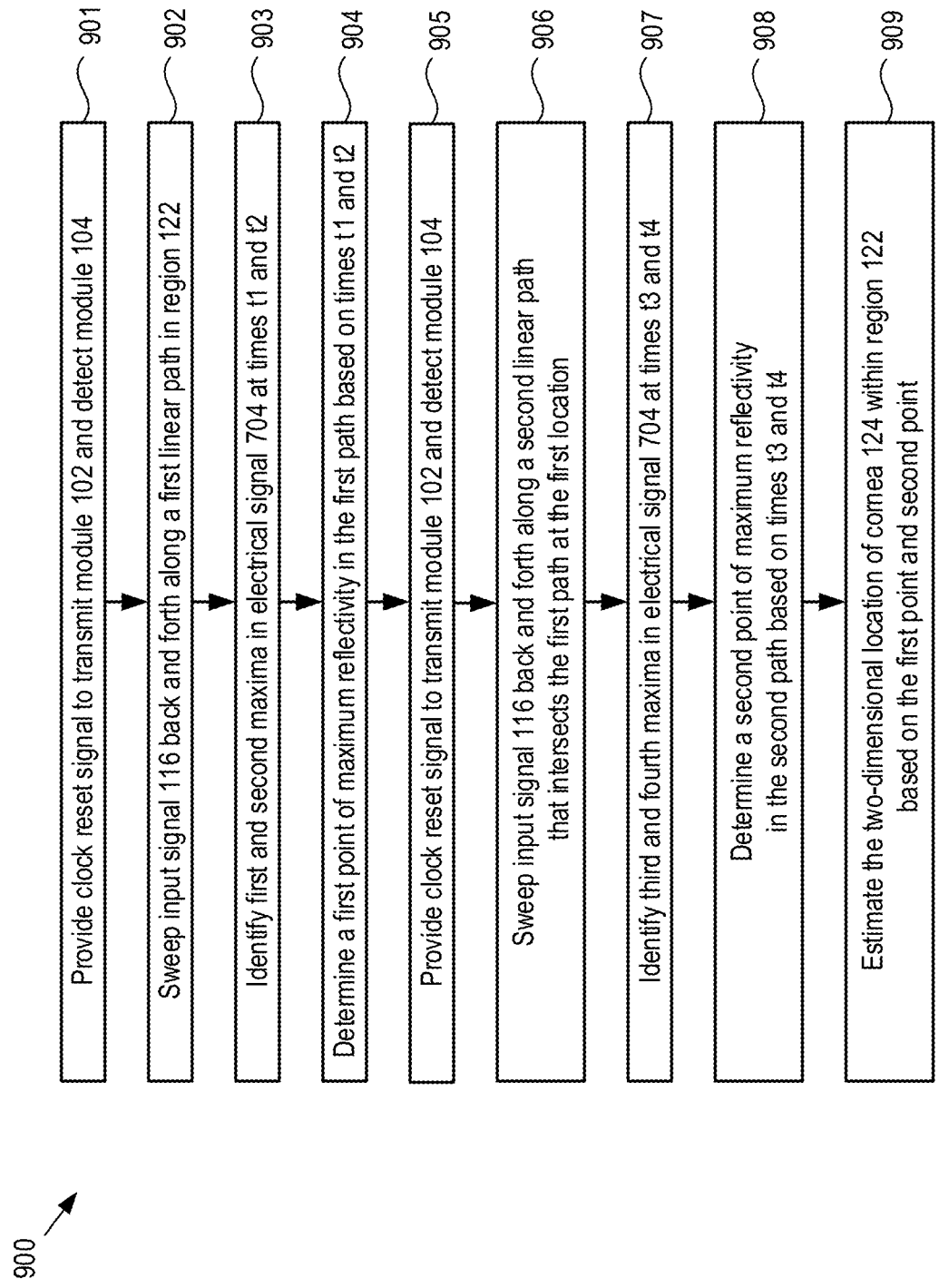
FIG. 9 depicts operations of a method suitable for tracking the position of a surface feature of an eye in accordance with the illustrative embodiment of the present invention.

FIG. 9 depicts operations of a method suitable for tracking the position of a surface feature of an eye in accordance with the illustrative embodiment of the present invention. Method 900 begins with operation 901, wherein clock reset signal R1 is provided to transmit module 102 and detect module 104 on control signal 128. Clock reset signal R1 restarts a system clock within processor 106 at time t0 and signals to transmit module 102 that it should direct input beam to an initial position on a first path through scan region 122.

Figure 10:
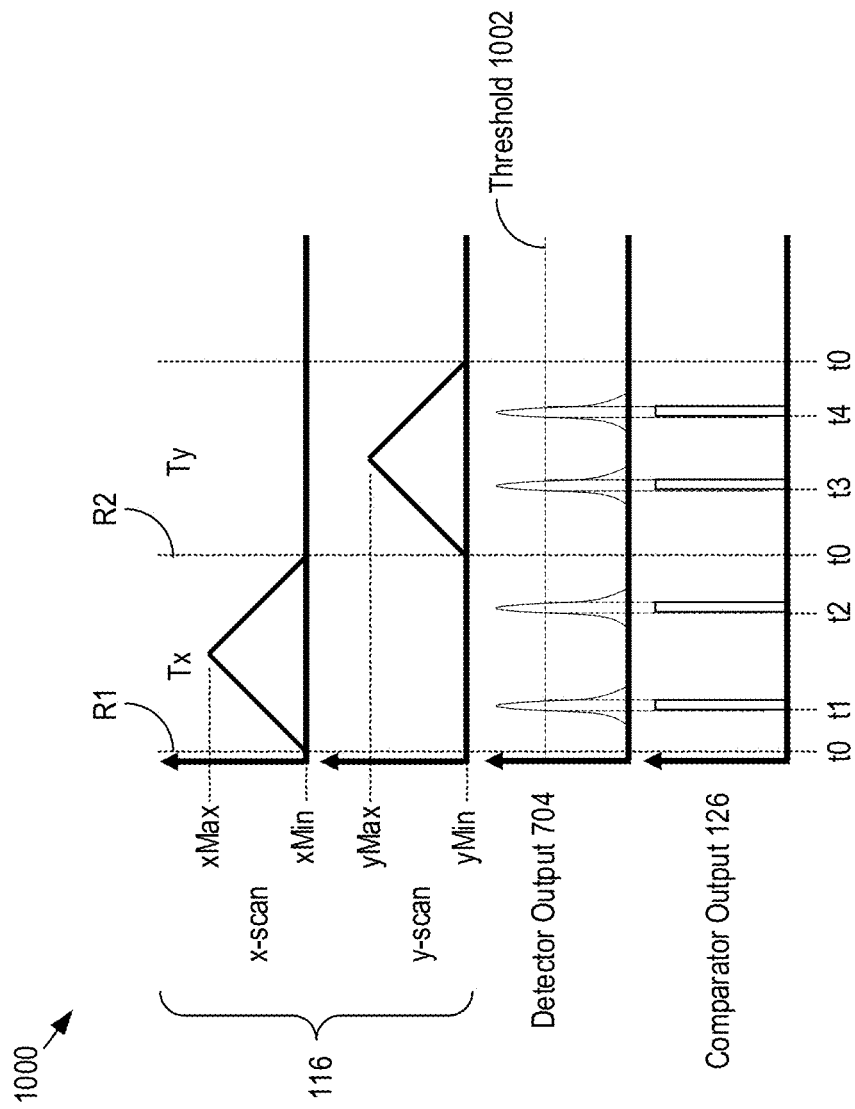
FIG. 10 depicts an exemplary timing diagram in accordance with method 900.

FIG. 10 depicts an exemplary timing diagram in accordance with method 900. Plot 1000 shows: (1) the position of input signal 116 along each of the x- and y-directions within scan region 122; (2) the magnitude of electrical signal 704; and (3) the magnitude of output signal 126 (i.e., the output of a comparator included in detection circuit 704)—each as a function of time, t.

At operation 902, input signal 116 is swept at a constant speed back and forth along a first path. Typically, the first path is located along the y-direction such that it includes the initial point, as discussed above. In the depicted example, the first path is a linear path aligned with the x-axis and substantially centered on the y-axis (i.e., midway between yMin and yMax as indicated in FIG. 2B). In some embodiments, the first path is another path through scan region 122. In some embodiments, the first path is linear path that is unaligned with either of the x- and y-axes.

At operation 903, first and second maxima (i.e., peaks) in electrical signal 704 are identified. As indicated in plot 1000, the first peak occurs at time t1, which arises during the first half of period Tx as input signal 116 travels in the positive x-direction. In similar fashion, the second peak occurs at time t2, which arises during the second half of period Tx as input signal 116 travels in the negative x-direction. The speed at which input beam 116 is swept across scan region 122 is preferably higher than the speed at which eye 120 can move. As a result, the first and second peaks correspond to the same corneal location within the scan region.

In the example depicted in plot 1000, times t1 and t2 correspond to the point at which the rising edge of electrical signal 704 exceeds comparator threshold 1002. In some embodiments, another feature of electrical signal 704 is used to determine times t1 and t2, such as the point at which the falling edge of electrical signal 704 decreases below comparator threshold 1002, or the midpoint between the points at which the rising and falling edges cross threshold 1002, etc. Typically, the detection of the timing of an edge of a pulse is less susceptible to noise than detecting the positions of the apex of a peak. Further, the resolution of detection circuit 702 improves as clock speed is increased. Still further, additional improvement in system SNR can be gained by modulating input signal 116 and demodulating electrical signal 704.

At operation 904, a first point of maximum reflectivity on the first path is estimated based on the time interval between times t1 and t2. Since input signal 116 is swept at a constant speed, the time interval between times t1 and t2 indicates the distance the input signal has traveled between peaks and, therefore, can be used to determine the point of maximum reflectivity along the first path.

At operation 905, clock reset signal R2 is provided to transmit module 102 and detect module 104. Clock reset signal R2 restarts the system clock at time t0 and signals to transmit module 102 that it should direct input beam to an initial position on a second path through scan region 122, where the second path includes the first point of maximum reflectivity on the first path. Typically, although not necessarily, the second path is a linear path that is orthogonal to the first path. In the depicted example, therefore, the second path is aligned with the y-axis.

At operation 906, input signal 116 is swept at constant speed back and forth along the second path between yMin to yMax At operation 907, third and fourth peaks in electrical signal 704 are identified. As indicated in plot 1000, the third peak occurs at time t3, which arises during the first half of period Ty as input signal 116 travels in the positive y-direction. In similar fashion, the fourth peak occurs at time t4, which arises during the second half of period Ty as input signal 116 travels in the negative y-direction.

At operation 908, a second point of maximum reflectivity on the second path is estimated based on the time interval between times t3 and t4. Since input signal 116 is swept at a constant speed in the y-direction, the time interval between times t3 and t4 indicates the distance the input signal has traveled between maxima and, therefore, the point of maximum reflectivity along the second path.

At operation 909, a two-dimensional location of cornea 124 within scan region 122 is estimated based on the points of maximum reflectivity on the first and second paths.

By continuously repeating method 900, the location of cornea 124 within scan region 122 can be constantly tracked.

Although mirror 502 is scanned at constant speed in the illustrative embodiment, it will be clear to one skilled in the art, after reading this Specification, how to specify, make, and use alternative embodiments of the present invention wherein mirror 502 is scanned using an alternative scanning method. Furthermore, in some embodiments, position is estimated by methods other than detecting the timing of pulses. For example, in some embodiments, a sinusoidal signal is used to excite the scanner at high speeds, while peak positions are estimated with a $sin^{-1}$ factor. In other embodiments, the actual position of mirror 502 at which a maximum occurs is used directly based on the voltages provided by processor 106 in control signal 128. In some embodiments, the position of mirror 502 is detected via a sensor that is operatively coupled with scanner 202.

It should be noted that method 900 has the disadvantage that abrupt changes in the micromirror position can result in mechanical ringing in the position of mirror 502. Such ringing can give rise to a limit on the speed and resolution that may be obtained with system 100.

Figure 11:
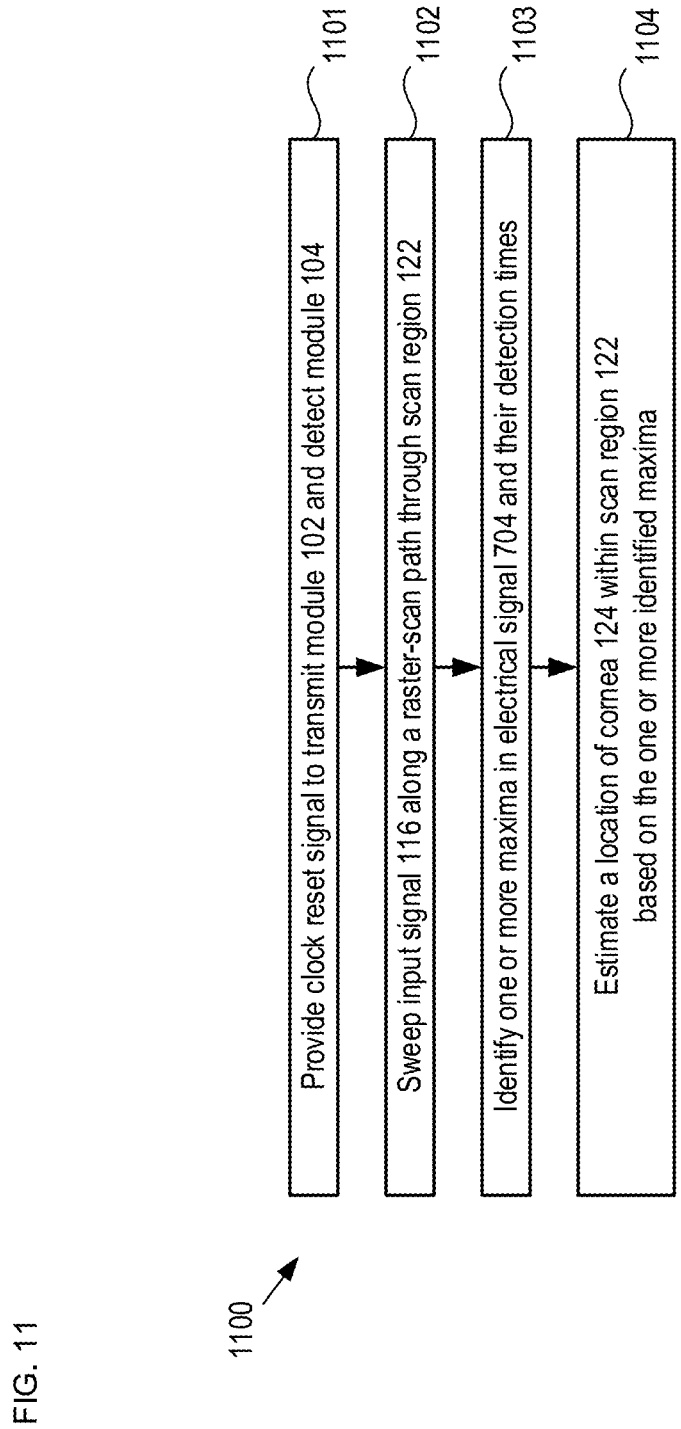
FIG. 11 depicts operations of a second exemplary method suitable for tracking the position of a surface feature of an eye in accordance with the present invention.

FIG. 11 depicts operations of a second exemplary method suitable for tracking the position of a surface feature of an eye in accordance with the present invention. Method 1100 begins with operation 1101, wherein a global clock reset signal is provided to transmit module 102. The global clock reset signal indicates the beginning of a raster scan period during which the entirety of scan region 122 is to be interrogated.

At operation 1102, input signal 116 is scanned at a constant rate of speed along a raster-scan path through scan region 122. In some embodiments, the scan rate along the x-direction is different than the scan rate along the y-direction.

In some embodiments, a different two-dimensional scanning path is used in operation 1102. Scanning paths suitable for use in embodiments of the present invention include, without limitation, Lissajous patterns, rhodonea curves, circular paths, elliptical paths, and the like. It should be noted that, when using continuous two-dimensional paths through scan region 122 (e.g., Lissajous patterns and rhodonea curves), the timing of the maxima in electrical signal 704 reveals information about the x and y position of cornea 124. In some embodiments, the trajectory of mirror 502 is offset in order to maintain a constant phase relationship between peaks. In some embodiments, the phase difference between the steady-state signals applied to each axis is adjusted to "sweep" the two-dimensional pattern over the eye. A drawback of two-dimensional scanning of scan region 122 is a reduction in the bandwidth of system 100.

As discussed above, in some embodiments, input signal 116 is formed as a crosshair pattern on eye 120. This is particularly advantageous for two-dimensional scanning approaches because such a light pattern virtually ensures that input signal 116 will traverse the point of maximum reflectivity.

At operation 1103, a plurality of maxima (i.e., peaks) in electrical signal 704, and their corresponding detection times, are identified.

At operation 1104, the location of input beam 116 corresponding to the peak having the largest magnitude is determined.

In some embodiments, the location of input beam 116 corresponding to the peak having the largest magnitude is used to estimate the location of cornea 124 in the y-direction, while the timing between adjacent peaks in at least one x-direction scan portion is used to estimate the location of cornea 124 in the x-direction.

Figure 12:
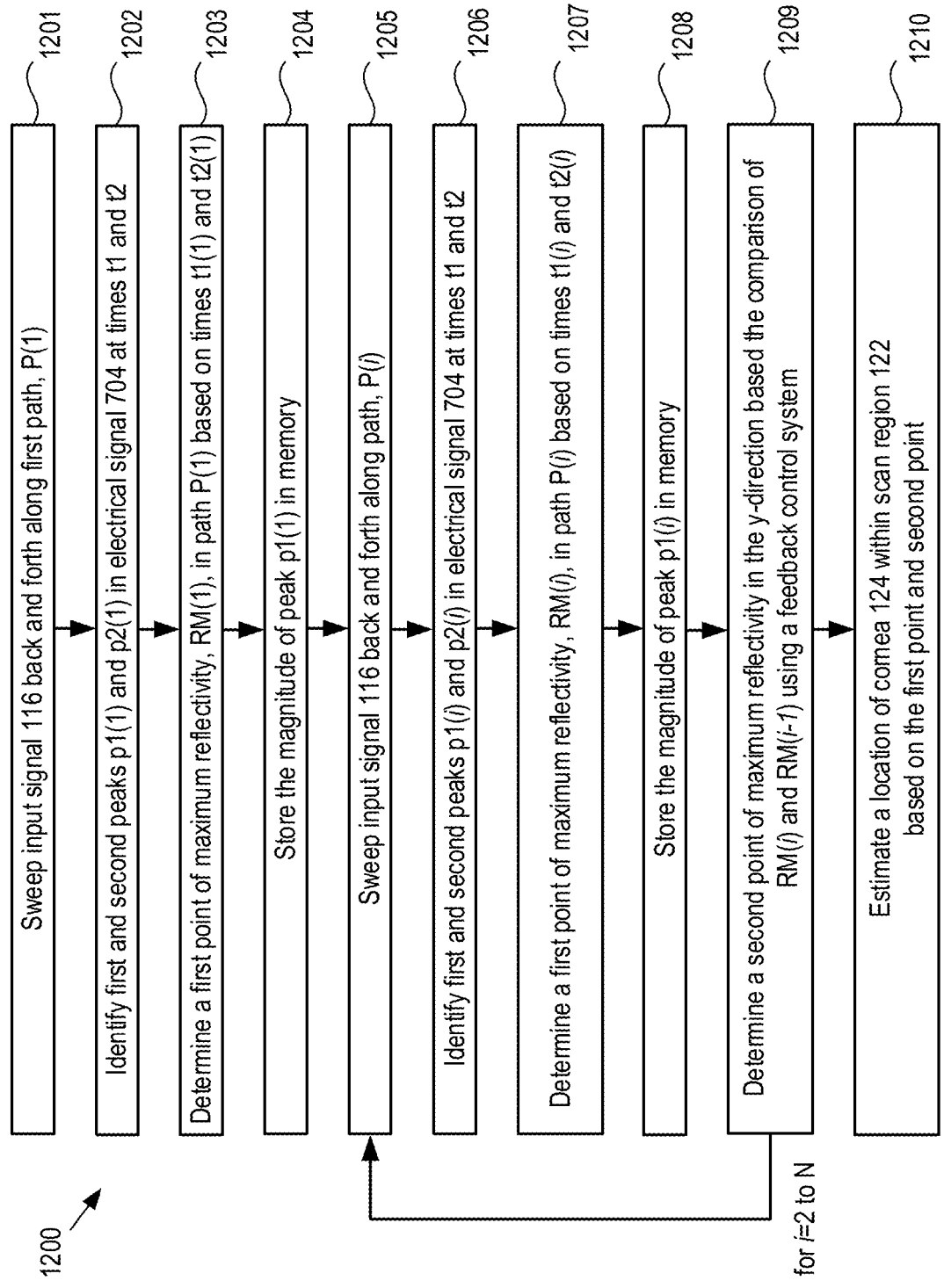
FIG. 12 depicts operations of a third exemplary method suitable for tracking the position of a surface feature of an eye in accordance with the present invention.

FIG. 12 depicts operations of a third exemplary method suitable for tracking the position of a surface feature of an eye in accordance with the present invention. Method 1100 employs the back-and-forth scanning approach to identify the point of maximum reflection in a first dimension, while simultaneously using a feedback control system to identify the point of maximum reflectivity in a second dimension that is orthogonal to the first dimension. In the depicted example, the first dimension is the x-direction and the second dimension is the y-direction. For the purposes of this Specification, including the appended claims, a "feedback control system" is defined as system of elements or commands that manages the operation of an eye-tracking system based on one or more measurements of the system output over time. Examples of feedback control systems in accordance with this definition include proportional-integral-derivative controllers (PID controllers), for proportional-summation-difference controllers (PSD controllers), hill-climbing controllers, Kalman Filters, and the like.

Method 1200 begins with operation 1201, wherein input signal 116 is swept at a constant speed back and forth along a first path, P(1). Typically, the P(1) is located along the y-direction such that it includes the initial point, as discussed above. In the depicted example, the first path is a linear path aligned with the x-axis and includes the initial point, IP, as discussed above. In some embodiments, the first path is another path through scan region 122. In some embodiments, the first path is linear path that is unaligned with either of the x- and y-axes.

At operation 1202, first and second peaks, p1(1) and p2(1) in electrical signal 704 are identified, as are times t1(1) and t2(1) at which they are detected.

At operation 1203, the point of maximum reflectivity, RM(1), in path P(1) is determined based on times t1(1) and t2(1).

At operation 1204, the magnitude of peak p1(1) is stored in memory. Note that the magnitudes of the peaks within a single scan line are substantially identical, as a result, the choice of which of peaks p1(1) and p2(1) to store is arbitrary.

For i=2 through N, where N is an arbitrary number:

At operation 1205, wherein input signal 116 is swept at a constant speed back and forth along a first path, P(i), where P(i) is offset from P(1) along the y-direction by an arbitrary distance.

At operation 1206, first and second peaks, p1(i) and p2(i) in electrical signal 704 are identified, as are times t1(i) and t2(i) at which they are detected.

At operation 1207, the point of maximum reflectivity in path P(i) is determined based on times t1(i) and t2(i).

At operation 1208, the magnitude of peak p1(i) is stored in memory.

At operation 1209, A second point of maximum reflectivity in the y-direction is determined by comparing RM(i) and RM(i−1) via a feedback control system.

At operation 1210, a location of cornea 124 within scan region 122 is determined based on the first point and second point.

It should be noted that, while the embodiments described herein are directed toward eye-tracking applications, the present invention can be directed at many alternative applications, such as head tracking, virtual keyboards based on finger tracking, and free-space communications links, among others.

In an exemplary head-tracking system in accordance with the present invention, a beam of light is directed from the head of a test subject toward a display (or other object). A small retro-reflector placed on the object reflects the beam of light back toward a scanner (e.g., scanner 202). Detector 204 is located adjacent to scanner 202 such that it can detect the reflected light. A timing circuit is used to estimate the orientation of the test subject's head with respect to the object. By including a second retroreflector, both the position and orientation of the test subject's head can be estimated.

A virtual keyboard in which the position of one or more fingers in contact with an arbitrary flat surface is also enabled by the present invention. In an exemplary virtual keyboard system, the surface is scanned with a narrow interrogation signal at a glancing angle. As a result, light reflected and scattered from the surface is not directed back towards the source. A photodetector is aligned flush with the surface, and an aperture restricts light that is incident on the photodetector. Only light that is directed substantially along the surface is detected, therefore. By performing a raster scan of the surface, the two-dimensional position of the one or more fingers in contact with the surface can be estimated.

The present invention also enables a free-space optical communications link comprising at least two nodes, where each node comprises at least one scanner, one retroreflector and one detector. A data-modulated beam of light directed from a first node towards a second node is directed back toward the detector of the first node by the retroreflector on the second node. Translation of the second node (for example, if the node is located on top of a building that sways due to wind or other forces) would normally reduce the intensity of the reflected beam. In accordance with the present invention, however, the scanner in the first node can track the position of the second node by monitoring the reflected power via its detector. Once the link is established, network traffic may be modulated onto the free-space optical link. An ad-hoc network can be formed with an arbitrary number of nodes, therefore, and can adapt to the addition or removal of nodes. When a two-way link is formed between two nodes, the power from one incoming beam can be transmitted as data (overhead) through the link and used for robust mutual tracking.

At this point we note that a system and accompanying method(s) for tracking eye movements has been disclosed and described. More particularly, a scanning microelectromechanical system (MEMS) positions a diffractive element to direct a beam of light towards an eye of a user. This beam reflects from the surface of the user's cornea onto a photodiode at a unique angle that is used to ascertain the user's gaze direction. As described, the system(s) and accompanying method(s) are at least an order of magnitude faster, lower power, more precise, and lower cost than prior-art, video-based system(s) and method(s).

A further advance is made according to aspects of the present invention, which advantageously employs a vertical tracking methodology and method(s) to track eye movement. As described previously, horizontal tracking is performed by scanning the beam of light in the x-direction, and detecting a pulse (i.e., volts) from the photodiode. This "edge tracking" method employs a timer to estimate the position of the eye based on the position of the scanner when the pulse is measured.

In contrast, a robust method according to aspects of the present invention tracks the vertical position of the eye through the use of an envelope detector that holds a peak value of the photodiode during a linescan in the x-direction. More particularly, as a raster scan pattern progresses downwards over the eye in the y-direction, the envelope emerges as a bell-curve-like intensity profile.

Figure 13:
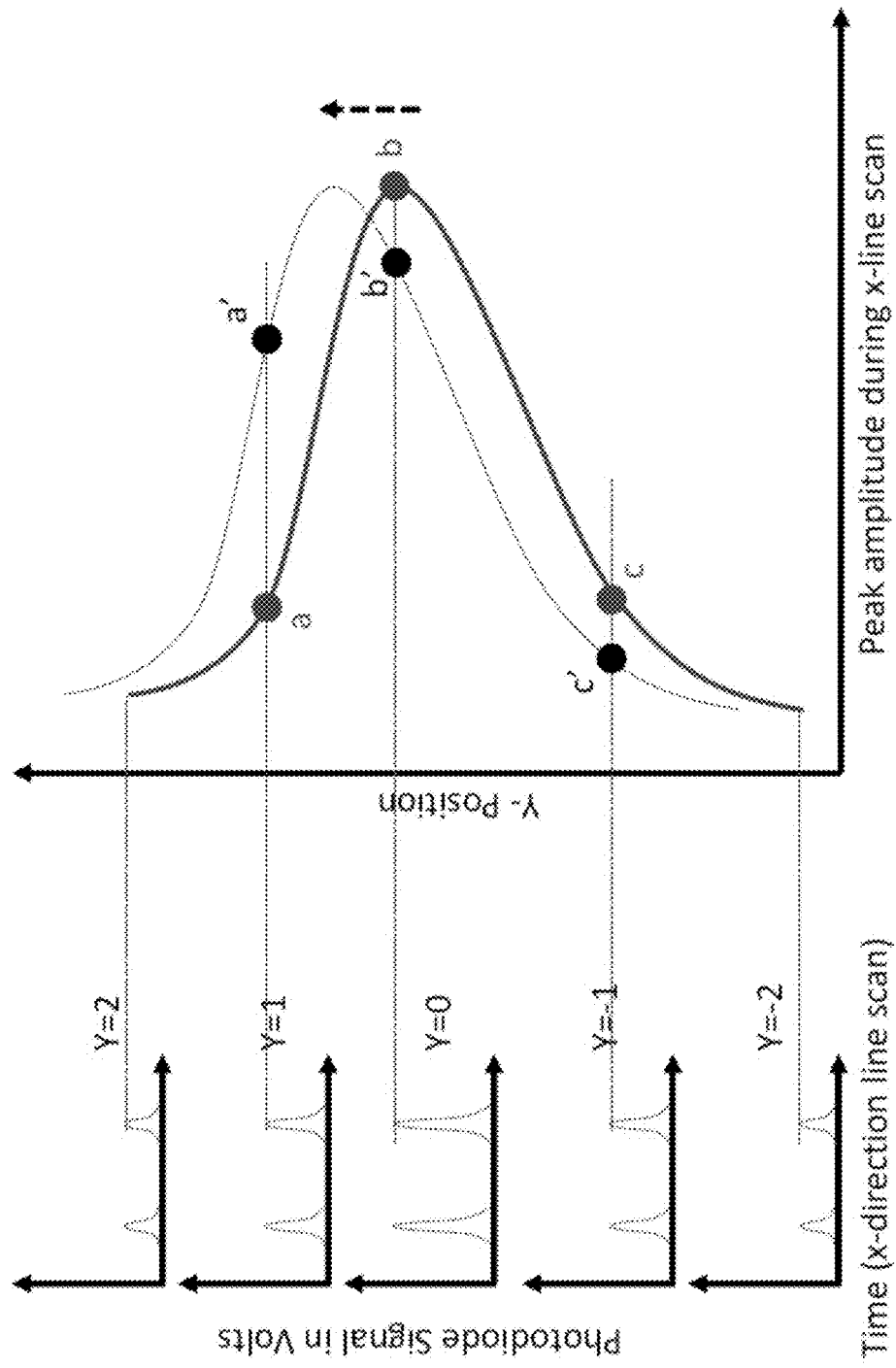
FIG. 13 is a plot of photodiode signal (volts) vs. Time compared with Y-position vs. peak amplitude during x-line scan for an improved vertical tracking according to aspects of the present invention.

FIG. 13 is a plot of photodiode signal (volts) vs. Time compared with Y-position vs. peak amplitude during x-line scan for an improved vertical tracking methodology according to aspects of the present invention. With reference to that FIG. 13, it may be observed that points a, b, and c correspond to the peak intensity values held by the envelope detector as the scanner traverses the eye in the vertical (y) direction. Point "b" corresponds to the maximum intensity, while points "a" and "c" correspond to neighboring intensity values. Notably, if the eye moves in the vertical direction, the intensity profile shifts upwards (black dashed curve). In this new position represented by the dashed curve, the new peak intensity values are indicated by "a'", "b'", and "c'". As may be observed from FIG. 13, a small vertical movement of the eye results in a large change in the measured difference in intensity between points a' and c' relative to the initial difference in intensity between a and c. Accordingly, a controller that minimizes the intensity difference between a' and c' will exhibit a high SNR according to aspects of the present invention.

Figure 14:
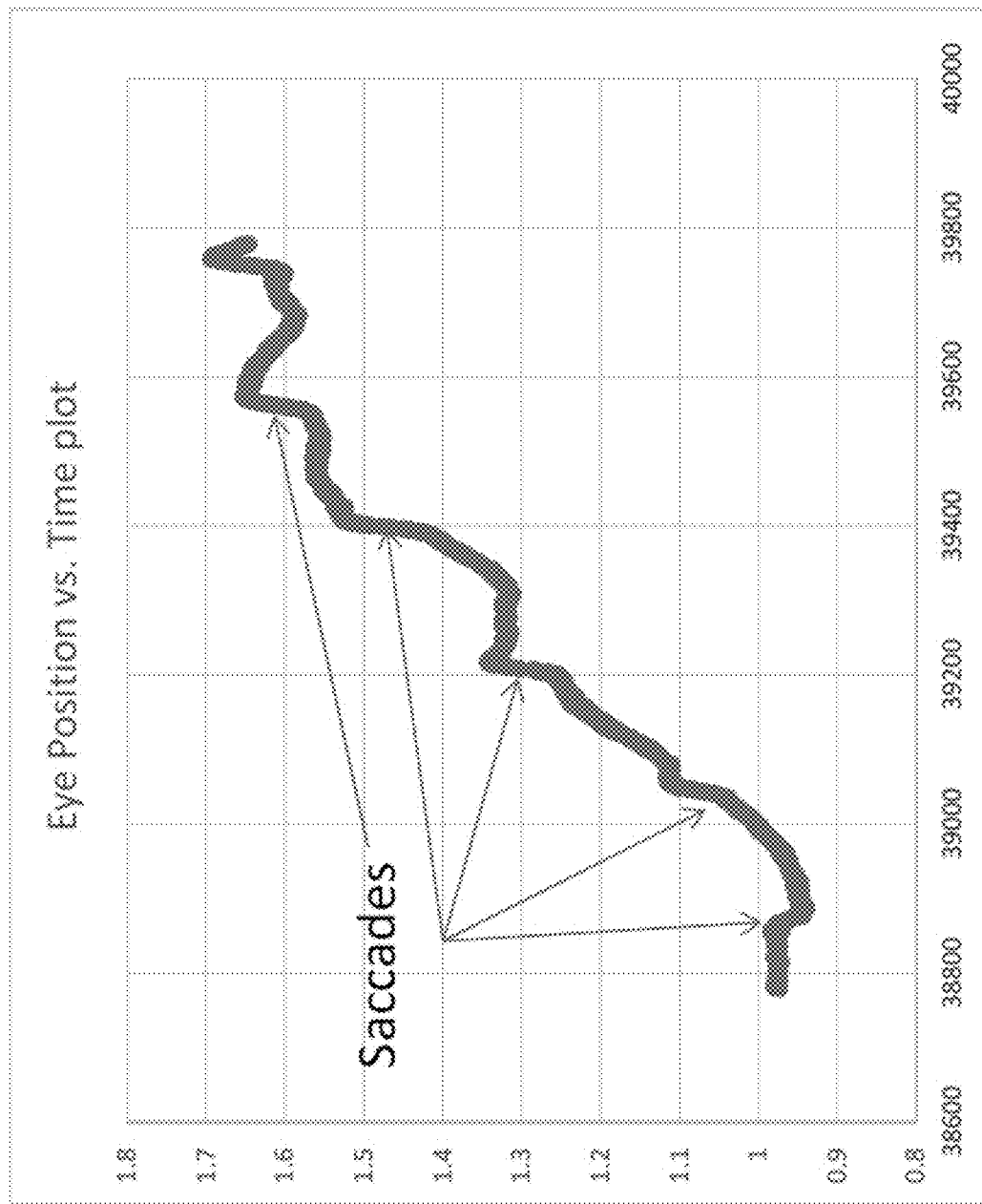
FIG. 14 is a plot of eye position vs. Time with saccades identified according to aspects of the present invention.

Advantageously, if the MEMS device is operated at its natural frequency, the position of the eye may be measured much faster than through the use of camera-based systems. FIG. 14 is a plot of eye position vs. Time with saccades identified according to aspects of the present invention. While not specifically shown in that figure, the data represented in that figure is obtained at substantially 875 Hz, and is generally limited by serial communication bandwidth (system produces measurements at substantially 3.3 kHz).

Figure 15:
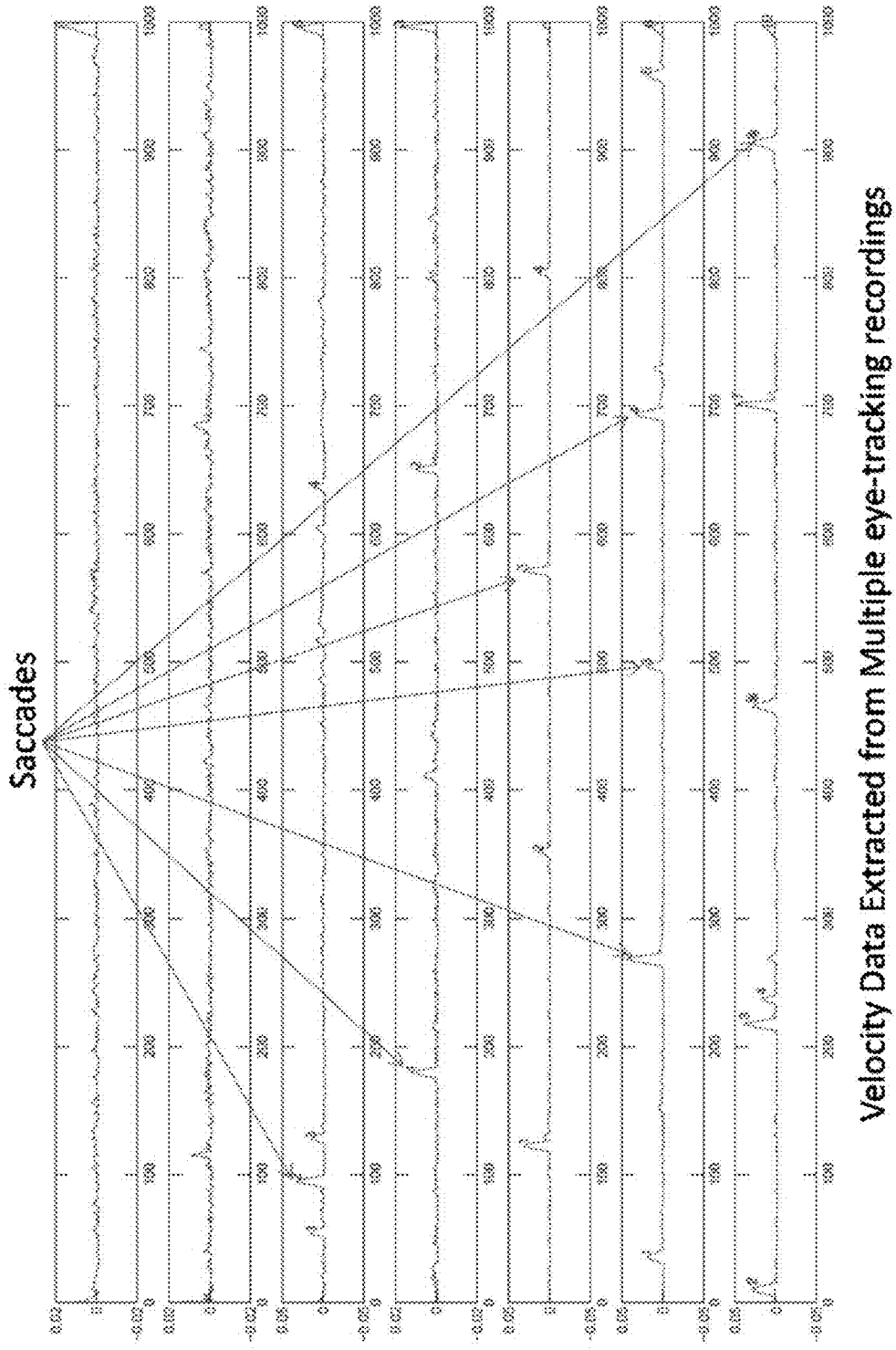
FIG. 15 is a series of plots of eye velocity data extracted from multiple eye-tracking recordings with saccades identified according to aspects of the present disclosure.
Figure 16:
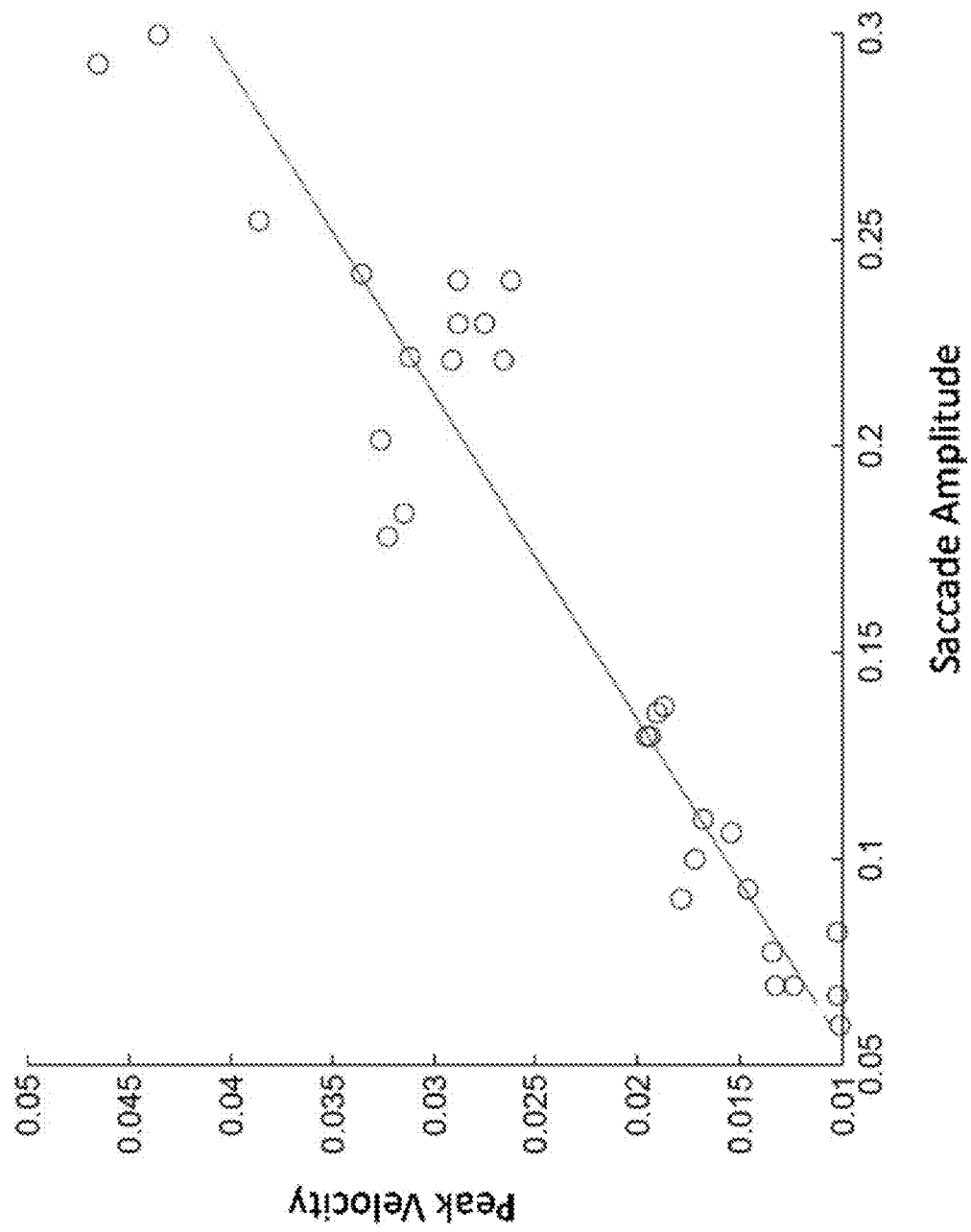
FIG. 16 is a plot of peak velocity vs. saccade amplitude according to aspects of the present invention.

As will be readily appreciated by those skilled in the art, such high speed measurements enable the observation of saccadic eye movements with high fidelity. Accordingly, if one compares the velocity of the eye such as that shown graphically in FIG. 15—which is a series of plots of eye velocity data extracted from multiple eye-tracking recordings with saccades identified according to aspects of the present invention—one observes peaks corresponding to these saccadic movements. Interestingly, there is a substantially linear relationship between the peak velocity of a particular saccade and it's amplitude (the angle that it subtends) as shown graphically in FIG. 16—which is a plot of peak velocity vs. saccade amplitude according to aspects of the present invention. This relationship has been measured with "high-end" eye trackers in numerous eye movement studies. In video-based eye tracking, the frame rate may be up to 1000 fps, but a latency exists between the image capture and the availability of post-processed eye-position data.

Of particular advantage, in systems and methods according to aspects of the present disclosure, the position data is available substantially instantly (within the bandwidth of the serial communication line—approximately 1 microsecond). Once the peak velocity has been reached, the amplitude of the saccade—and therefore the final position of the eye after the saccade—may be estimated with a high degree of accuracy. Of further advantage, the estimate may be performed with minimal computation, and yields a result ~25 ms (25,000,000 clock cycles of a 1 GHz processor) before the end of the saccade. The result is a "negative latency" eye tracking measurement. As will be readily appreciated by those skilled in the art, this capability—provided by methods and systems according to aspects of the present disclosure—is particularly attractive in "Virtual Reality" and/or "Augmented Reality" systems and methods—where "foveated rendering" stands to dramatically improve latency and computational expense.

Figure 17:
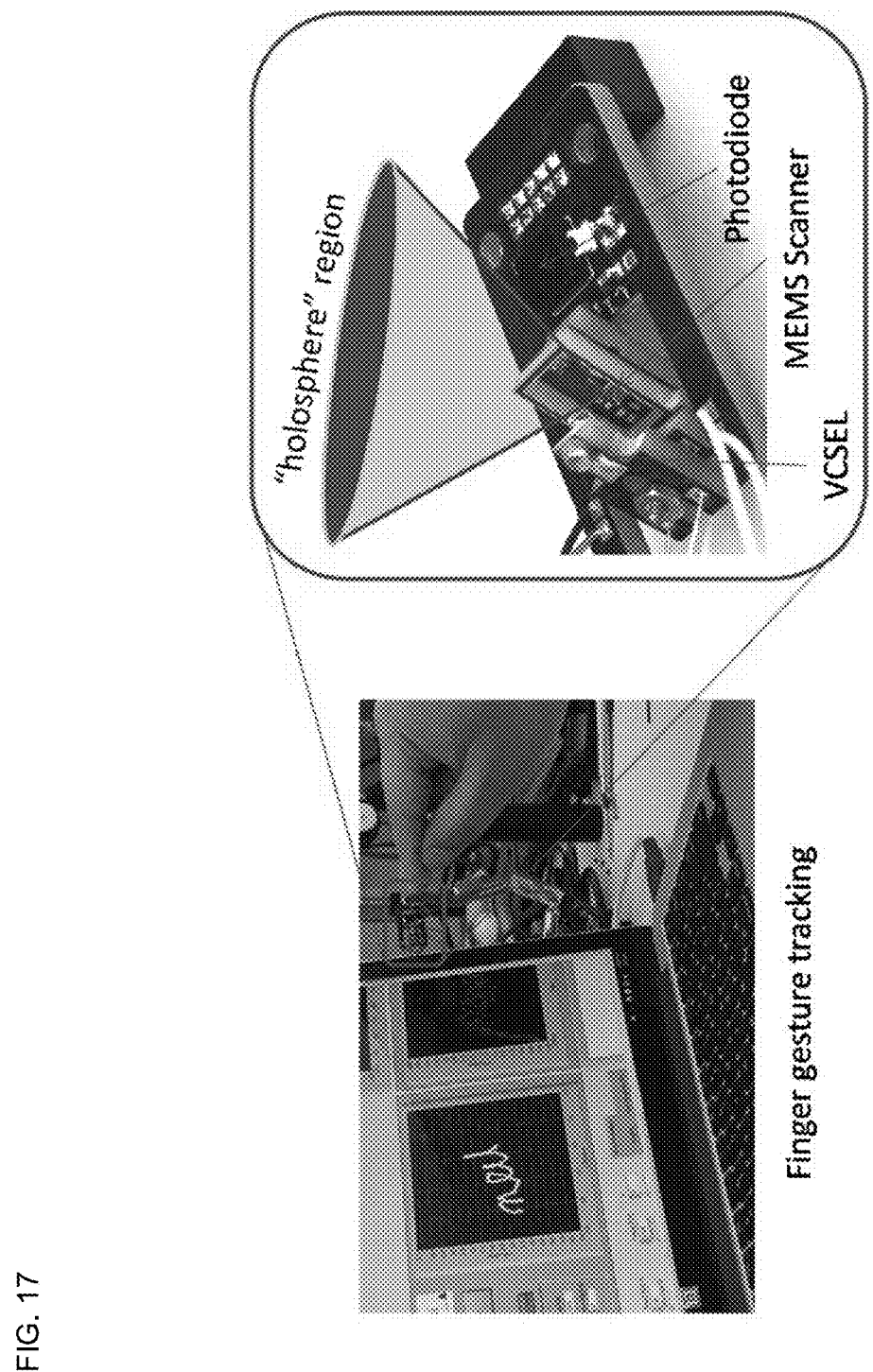
FIG. 17 is an illustration of finger gesture tracking and system including VCSEL, MEMS Scanner, and photodiode with identified "holosphere" region according to aspects of the present invention.

Finally, we note that FIG. 17 is an illustration of finger gesture tracking and system including VCSEL, MEMS Scanner, and photodiode with identified "holosphere" region according to aspects of the present invention. As will be further understood and greatly appreciated by those skilled in the art, the geometric arrangement that is favorable for eye tracking may be modified to track other objects. A prototype scanner module shown in FIG. 17 projects a beam that is scanned over a hemisphere defined by the MEMS scan range. An object (e.g., a human finger) in the hemisphere reflects the beam towards a photodetector. The position of the object may be estimated using methods and/or algorithms like or otherwise similar to those disclosed for eye-tracking. In addition, the distance of the object from the sensor may be estimated based on the peak amplitude of the finger tracing out a word. As will be readily appreciated by those skilled in the art, the VCSEL, MEMS scanner, photodiode is advantageously integrated into a very small (i.e., 1 mm×0.5 mm×0.5 mm—or smaller) surface mount package through wafer-scale techniques according to yet other aspects of the present invention.

Operationally, method(s) providing illustrative examples and/or particular aspects of the present invention may be conveniently described. With particular respect to vertical tracking:

Illustrative Vertical Tracking a) place the fast (resonant) axis of the MEMS device in mechanical resonance. Advantageously, resonance may be detected by any of a variety of methods including via integrated piezoresistors or optically by overscanning such that the photodiode is directly illuminated by the scanner module.

b) start a timer in-phase with a signal that drives the fast axis, consider this a first line.

c) when the voltage from the photodetector exceeds a threshold value (pulse detected) capture the timer value—report this as the x-position.

d) when the fast-axis drive signal completes 1 cycle (360 degrees), capture the maximum value from the photodiode using the peak-hold circuit—sample this value with an ADC and set the photodiode threshold to ½ of this value.

e) increment vertical position by "i" to scan a second line. Repeat steps a-d.

f) increment vertical position by "i" to scan a third line. Repeat steps a-d.

g) confirm that the amplitude captured over the second line is greater than the first and third lines.

h) If yes, report the y-direction global maximum by offsetting the location of the second line by a factor corresponding to the difference between the first and third line amplitudes (curve fitting).

i) offset the y-position by "j" where j is the output of a PID controller with an error term $=(1^{st}$ line amplitude-$3^{rd}$ line amplitude)

perform steps b-i.

Predictive Eye Tracking a) perform an n-point moving average of the position measurements from the eye tracker method using a cyclic buffer.

b) divide the value by the sampling time to obtain a velocity value.

c) if the velocity exceeds a threshold, we are entering a "Saccade"—store the position.

d) continue calculating the velocity until the acceleration changes sign (peak velocity reached)

e) based on the starting point and peak velocity, calculate the end position of the saccade (magnitude of vector from beginning to end of saccade is proportional to peak velocity, direction is set by location of start position and peak velocity.

Finger Tracking

Finger tracking methods according to the present invention is similar to that of eye tracking. Peak amplitude captured global maximum line is used as a measure of z-distance. The geometric configuration of the scanner module and photodiode is re-arranged so that they are co-located in order to capture the specular reflection from the object that is being tracked.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A method of tracking eye movement comprising:
   generating an intensity profile of the eye the generating including:
   scanning an optical signal on the surface of the eye such that a portion of the optical signal is reflected; and
   generating an electrical signal from the reflected optical signal wherein the electrical signal excludes spatially correlated image information;
   determining saccadic eye movement from the generated intensity profile; and
   estimating, during the saccadic eye movement, a position of the eye after the saccadic movement.

2. The method of claim 1 further comprising:
   generating a second intensity profile of the eye; and
   comparing the intensity profile to the second intensity profile;
   wherein said eye movement is determined from any comparative differences in the intensity profiles.

3. The method of claim 1 wherein said intensity profile is generated through the effect of a raster scan process.

4. The method of claim 2 further comprising determining the saccadic eye movement from the comparative differences.

5. The method of claim 4 further comprising determining a velocity of the eye movement.

6. The method of claim 5 wherein the estimated position is an unmoving position of the eye after the saccade.

7. The method of claim 1 further comprising:
   directing a laser light to the eye; and
   detecting laser light reflected from the eye.

8. The method of claim 7 wherein the intensity profile is determined from the reflected laser light.

* * * * *